(12) United States Patent
Witowski et al.

(10) Patent No.: US 12,396,982 B2
(45) Date of Patent: *Aug. 26, 2025

(54) COMPOSITIONS OF MATTER AND PHARMACEUTICAL COMPOSITIONS

(71) Applicant: Atai Therapeutics, Inc., New York, NY (US)

(72) Inventors: Christopher G. Witowski, Tampa, FL (US); Jacqueline L. Salm, Tampa, FL (US)

(73) Assignee: Atai Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/744,484

(22) Filed: Jun. 14, 2024

(65) Prior Publication Data

US 2025/0041273 A1 Feb. 6, 2025

Related U.S. Application Data

(63) Continuation of application No. 18/229,286, filed on Aug. 2, 2023, now Pat. No. 12,053,453, which is a continuation of application No. 17/314,107, filed on May 7, 2021, now Pat. No. 11,759,452.

(60) Provisional application No. 63/134,805, filed on Jan. 7, 2021, provisional application No. 63/106,516, filed on Oct. 28, 2020, provisional application No. 63/021,866, filed on May 8, 2020.

(51) Int. Cl.
| | |
|---|---|
| *A61K 31/4045* | (2006.01) |
| *A61K 9/00* | (2006.01) |
| *A61K 9/06* | (2006.01) |
| *A61K 9/20* | (2006.01) |
| *A61K 9/70* | (2006.01) |
| *A61K 31/405* | (2006.01) |
| *A61K 31/48* | (2006.01) |
| *A61K 31/55* | (2006.01) |
| *A61K 31/675* | (2006.01) |
| *C07D 209/16* | (2006.01) |

(52) U.S. Cl.
CPC ........ *A61K 31/4045* (2013.01); *A61K 9/0043* (2013.01); *A61K 9/06* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/7061* (2013.01); *A61K 9/7069* (2013.01); *A61K 31/405* (2013.01); *A61K 31/48* (2013.01); *A61K 31/55* (2013.01); *A61K 31/675* (2013.01); *C07D 209/16* (2013.01)

(58) Field of Classification Search
CPC .... A61K 31/4045; A61K 9/0043; A61K 9/06; A61K 9/2009; A61K 9/2013; A61K 9/2018; A61K 9/2027; A61K 9/2054; A61K 9/7061; A61K 9/7069; A61K 31/405; A61K 31/48; A61K 31/55; A61K 31/675; C07D 209/16

USPC ........................................................ 514/415
See application file for complete search history.

(56) References Cited

U.S. PATENT DOCUMENTS

| | | | |
|---|---|---|---|
| 3,499,003 | A | 3/1970 | Welstead, Jr. |
| 3,594,391 | A | 7/1971 | Wolf et al. |
| 3,781,300 | A | 12/1973 | Wolf et al. |
| 4,252,803 | A | 2/1981 | Webb |
| 5,340,838 | A | 8/1994 | Gidda et al. |
| 5,347,029 | A | 9/1994 | Johnson |
| 5,637,593 | A | 6/1997 | Porter et al. |
| 5,705,527 | A | 1/1998 | Ishihara et al. |
| 6,201,025 | B1 | 3/2001 | Dax et al. |
| 6,403,808 | B1 | 6/2002 | Glennon et al. |
| 6,436,950 | B1 | 8/2002 | Achari et al. |
| 6,500,456 | B1 | 12/2002 | Capella |
| 8,268,856 | B2 | 9/2012 | Hamann et al. |
| 9,388,395 | B2 | 7/2016 | Nazor et al. |
| 9,549,942 | B2 | 1/2017 | Jo et al. |
| 10,064,856 | B2 | 9/2018 | Bosse et al. |
| 10,550,140 | B2 | 2/2020 | Wiles et al. |
| 11,242,318 | B2 | 2/2022 | Nivorozhkin et al. |
| 11,292,765 | B2 | 4/2022 | Bryson |
| 11,332,441 | B2 | 5/2022 | Chadeayne |
| 11,406,619 | B2 | 8/2022 | Layzell et al. |
| 11,478,449 | B1 | 10/2022 | Witowski et al. |
| 11,591,353 | B2 | 2/2023 | Slassi et al. |
| 11,602,521 | B2 | 3/2023 | Rao et al. |
| 11,643,391 | B2 | 5/2023 | Perni et al. |

(Continued)

FOREIGN PATENT DOCUMENTS

| | | |
|---|---|---|
| EP | 0 821 957 A2 | 2/1998 |
| EP | 1336602 A1 | 8/2003 |

(Continued)

OTHER PUBLICATIONS (National Center for Biotechnology Information) "[2-bromo-3-[2-(dimethylamino) ethyl]-1H-indol-4-yl] acetate: PUBCHEM CID 157042555" Pubchem entry (online), pp. 1-8, Nov. 30, 2021; Retrieved on Jul. 9, 2024 from the Internet: [URL: https://pubchem.ncbi.nlm.nih.gov/compound/157042555]; p. 2, see 2D structure.

(Continued)

*Primary Examiner* — Kristin A Vajda
(74) *Attorney, Agent, or Firm* — COOLEY LLP

(57) ABSTRACT

Pharmaceutical formulations of novel indole compounds and psilocybin analogs are manufactured, provided in novel oral, transdermal, and nasal pharmaceutical compositions for use to treat neurological, mood or abuse diseases and disorders.

20 Claims, 2 Drawing Sheets

(56) References Cited

U.S. PATENT DOCUMENTS

| | | |
|---|---|---|
| 11,759,452 B2 | 9/2023 | Witowski et al. |
| 12,012,381 B2 | 6/2024 | Perni et al. |
| 12,053,453 B2 * | 8/2024 | Witowski ............ A61K 9/2013 |
| 12,065,405 B2 | 8/2024 | Perni |
| 12,128,027 B2 | 10/2024 | Rao et al. |
| 2002/0052370 A1 | 5/2002 | Barber et al. |
| 2002/0115715 A1 | 8/2002 | Dax et al. |
| 2003/0079301 A1 | 5/2003 | Sauter et al. |
| 2004/0235899 A1 | 11/2004 | Maria Assunta et al. |
| 2005/0152858 A1 | 7/2005 | Bertz et al. |
| 2005/0245594 A1 | 11/2005 | Sutter et al. |
| 2005/0250839 A1 | 11/2005 | Marnett et al. |
| 2007/0099909 A1 | 5/2007 | Chen et al. |
| 2007/0140977 A1 | 6/2007 | Yoneto et al. |
| 2008/0248511 A1 | 10/2008 | Daily et al. |
| 2008/0306025 A1 | 12/2008 | Yu et al. |
| 2008/0318957 A1 | 12/2008 | Glinka et al. |
| 2009/0221549 A1 | 9/2009 | Gerber et al. |
| 2010/0113539 A1 | 5/2010 | Scott et al. |
| 2011/0245215 A1 | 10/2011 | Carrara et al. |
| 2012/0028995 A1 | 2/2012 | Ansorge et al. |
| 2012/0108510 A1 | 5/2012 | Young et al. |
| 2012/0122948 A1 | 5/2012 | Soubhye et al. |
| 2015/0071994 A1 | 3/2015 | Schentag et al. |
| 2015/0284365 A1 | 10/2015 | Elder et al. |
| 2015/0346226 A1 | 12/2015 | McConnell et al. |
| 2016/0002195 A1 | 1/2016 | Makriyannis et al. |
| 2016/0074411 A1 | 3/2016 | Krumpl |
| 2016/0106694 A1 | 4/2016 | Roberts et al. |
| 2016/0303079 A1 | 10/2016 | Hung |
| 2018/0221396 A1 | 8/2018 | Chadeayne |
| 2019/0315689 A1 | 10/2019 | Chen et al. |
| 2019/0345103 A1 | 11/2019 | Batchelor et al. |
| 2020/0199119 A1 | 6/2020 | Thompson et al. |
| 2020/0325124 A1 | 10/2020 | LaVoie et al. |
| 2020/0390746 A1 | 12/2020 | Rands et al. |
| 2020/0397752 A1 | 12/2020 | Perez Castillo et al. |
| 2021/0015738 A1 | 1/2021 | LaRosa et al. |
| 2021/0085671 A1 | 3/2021 | Chadeayne |
| 2021/0108238 A1 | 4/2021 | Protzko |
| 2021/0145851 A1 | 5/2021 | Stamets |
| 2021/0236523 A1 | 8/2021 | Schindler et al. |
| 2021/0277433 A1 | 9/2021 | Protzko |
| 2021/0292278 A1 | 9/2021 | Chadeayne |
| 2021/0322306 A1 | 10/2021 | Espinoza et al. |
| 2021/0322447 A1 | 10/2021 | Plakogiannis et al. |
| 2021/0346347 A1 | 11/2021 | Witowski et al. |
| 2021/0353615 A1 | 11/2021 | Chadeayne |
| 2021/0363104 A1 | 11/2021 | Nivorozhkin et al. |
| 2021/0378969 A1 | 12/2021 | Rands et al. |
| 2021/0395201 A1 | 12/2021 | Rands et al. |
| 2021/0403425 A1 | 12/2021 | Bryson |
| 2022/0015749 A1 | 1/2022 | Sanders et al. |
| 2022/0024956 A1 | 1/2022 | Slassi et al. |
| 2022/0031662 A1 | 2/2022 | Terwey |
| 2022/0071958 A1 | 3/2022 | Terwey |
| 2022/0079881 A1 | 3/2022 | Modi |
| 2022/0096504 A1 | 3/2022 | Blumstock et al. |
| 2022/0259147 A1 | 8/2022 | Feilding-Mellen |
| 2022/0267267 A1 | 8/2022 | Feilding-Mellen |
| 2022/0273628 A1 | 9/2022 | Liechti et al. |
| 2022/0304980 A1 | 9/2022 | Arnold et al. |
| 2022/0339139 A1 | 10/2022 | Rao et al. |
| 2022/0354824 A1 | 11/2022 | Witowski et al. |
| 2022/0388956 A1 | 12/2022 | Short et al. |
| 2023/0041584 A1 | 2/2023 | Perni et al. |
| 2023/0066720 A1 | 3/2023 | Perni et al. |
| 2023/0099972 A1 | 3/2023 | Rao et al. |
| 2023/0136824 A1 | 5/2023 | Rao et al. |
| 2023/0227407 A1 | 7/2023 | Perni et al. |
| 2023/0227421 A1 | 7/2023 | Perni et al. |
| 2023/0233537 A1 | 7/2023 | Dornbierer et al. |
| 2023/0310374 A1 | 10/2023 | Rao et al. |
| 2023/0321039 A1 | 10/2023 | Rao et al. |
| 2023/0322735 A1 | 10/2023 | Kruegel |
| 2023/0357146 A1 | 11/2023 | Perni et al. |
| 2023/0372295 A1 | 11/2023 | Witowski et al. |
| 2024/0116896 A1 | 4/2024 | Khan et al. |
| 2024/0199544 A1 | 6/2024 | Fawaz et al. |
| 2024/0287107 A1 | 8/2024 | Khan |
| 2024/0400511 A1 | 12/2024 | Perni et al. |
| 2024/0415811 A1 | 12/2024 | Gray |
| 2025/0002457 A1 | 1/2025 | Yacoub et al. |
| 2025/0064783 A1 | 2/2025 | Witowski et al. |

FOREIGN PATENT DOCUMENTS

| | | |
|---|---|---|
| WO | WO-9506638 A1 | 3/1995 |
| WO | WO-9524200 A1 | 9/1995 |
| WO | WO-9617842 A1 | 6/1996 |
| WO | WO-0041755 A1 | 7/2000 |
| WO | WO-0051672 A1 | 9/2000 |
| WO | WO-0211800 A2 | 2/2002 |
| WO | WO-02068029 A2 | 9/2002 |
| WO | WO-02068030 A2 | 9/2002 |
| WO | WO-02068031 A2 | 9/2002 |
| WO | WO-02068032 A2 | 9/2002 |
| WO | WO-03000310 A2 | 1/2003 |
| WO | WO-03020350 A1 | 3/2003 |
| WO | WO-03026559 A2 | 4/2003 |
| WO | WO-03082393 A1 | 10/2003 |
| WO | WO-03084591 A1 | 10/2003 |
| WO | WO-03090812 A2 | 11/2003 |
| WO | WO-2006099416 A1 | 9/2006 |
| WO | WO-2010151258 A1 | 12/2010 |
| WO | WO-2011041870 A1 | 4/2011 |
| WO | 2013/063492 A1 | 5/2013 |
| WO | 2018/064465 A1 | 4/2018 |
| WO | 2018/081456 A1 | 5/2018 |
| WO | WO-2018094106 A2 | 5/2018 |
| WO | WO-2018148605 A1 | 8/2018 |
| WO | WO-2019081764 A1 | 5/2019 |
| WO | WO-2019213551 A1 | 11/2019 |
| WO | WO-2020037372 A1 | 2/2020 |
| WO | 2020/181194 A1 | 3/2020 |
| WO | WO-2020169850 A1 | 8/2020 |
| WO | WO-2020169851 A1 | 8/2020 |
| WO | WO-2020176597 A1 | 9/2020 |
| WO | WO-2020212951 A1 | 10/2020 |
| WO | 2021/003467 A1 | 1/2021 |
| WO | 2021/168082 A1 | 8/2021 |
| WO | WO-2021155468 A1 | 8/2021 |
| WO | 2021/188782 A1 | 9/2021 |
| WO | 2021/226416 A1 | 11/2021 |
| WO | WO-2021226041 A1 | 11/2021 |
| WO | 2021/259962 A1 | 12/2021 |
| WO | WO-2021244831 A1 | 12/2021 |
| WO | WO-2021250434 A1 | 12/2021 |
| WO | WO-2021250435 A1 | 12/2021 |
| WO | WO-2022051670 A1 | 3/2022 |
| WO | WO-2022061242 A1 | 3/2022 |
| WO | WO-2022082058 A1 | 4/2022 |
| WO | WO-2022109050 A1 | 5/2022 |
| WO | WO-2022123232 A1 | 6/2022 |
| WO | WO-2022150675 A1 | 7/2022 |
| WO | WO-2022160056 A1 | 8/2022 |
| WO | WO-2022170442 A1 | 8/2022 |
| WO | WO-2022195011 A1 | 9/2022 |
| WO | 2022/243285 A1 | 11/2022 |
| WO | WO-2022232179 A1 | 11/2022 |
| WO | WO-2022235514 A1 | 11/2022 |
| WO | WO-2022235529 A1 | 11/2022 |
| WO | WO-2022246572 A1 | 12/2022 |
| WO | WO-2022251351 A1 | 12/2022 |
| WO | WO-2022261383 A1 | 12/2022 |
| WO | WO-2023283386 A2 | 1/2023 |
| WO | WO-2023021112 A1 | 2/2023 |
| WO | WO-2023036473 A1 | 3/2023 |
| WO | WO-2023055992 A1 | 4/2023 |
| WO | 2023076150 A1 | 5/2023 |
| WO | WO-2023076135 A1 | 5/2023 |
| WO | WO-2023078604 A1 | 5/2023 |
| WO | WO-2023111544 A2 | 6/2023 |
| WO | WO-2023115166 A1 | 6/2023 |

(56) References Cited

FOREIGN PATENT DOCUMENTS

| WO | WO-2023129956 | | 7/2023 |
| --- | --- | --- | --- |
| WO | WO-2024054866 | A2 | 3/2024 |
| WO | WO-2024092106 | A2 | 5/2024 |
| WO | WO-2024118767 | A2 | 6/2024 |
| WO | WO-2024119075 | A1 | 6/2024 |
| WO | WO-2024130140 | A2 | 6/2024 |
| WO | WO-2024130140 | A3 | 7/2024 |
| WO | WO-2024227149 | A2 | 10/2024 |
| WO | 2024/342488 | A2 | 11/2024 |
| WO | WO-2024243488 | A2 | 11/2024 |
| WO | WO-2025019800 | A1 | 1/2025 |
| WO | WO-2025024637 | A1 | 1/2025 |
| WO | WO-2025054397 | A1 | 3/2025 |

OTHER PUBLICATIONS (National Center for Biotechnology Information) "3-[2-(dimethylamino) ethyl]-2-fluoro-1H-indol-4-yl]acetate: PUBCHEM CID 162478146" Pubchem entry (online), pp. 1-8, Feb. 6, 2022; Retrieved on Jul. 9, 2024 from the Internet: [URL: https://pubchem.ncbi.nlm.nih.gov/compound/162478146); p. 2, see 2D structure.

(National Center for Biotechnology Information) "3-[2-(dimethylamino) ethyl)-2-fluoro-1H-indol-4-ol: PUBCHEM CID 162478135" Pubchem entry (online), pp. 1-8, Feb. 6, 2022; Retrieved on Jul. 9, 2024 from the Internet: [URL: https:f/pubchem.ncbi.nlm.nih.gov/compound/162478135);p. 2, see 2D structure.

(National Center for Biotechnology Information) "1-[3-[2-(dlmethylamino) ethyl]-1H-indol-4-yl]-N-methylmethanesulfonamlde: PUBCHEM CID 149771082" Pubchem entry (online), pp. 1-8, Aug. 12, 2020; Retrieved on Jul. 9, 2024 from the Internet: [URL: https://pubchem.ncbi.nlm.nlh.gov/compound/149771082); p. 2, see 2D structure.

(National Center for Biotechnology Information) "4-Acetoxy-N, N-diisopropyltryptamine: PUBCHEM CID 24801868" Pubchem entry (online), pp. 1-19, Jun. 6, 2008; Retrieved on Jul. 9, 2024 from the Internet: [URL: https:f/pubchem.ncbi.nlm.nih.gov/compound/24801868); p. 2, see 2D structure.

(National Center for Biotechnology Information) "N,N-Diisopropyl-4-methoxytryptamine: PUBCHEM CID 24802108" Pubchem entry (online), pp. 1-12, Jun. 6, 2008; Retrieved on Jul. 9, 2024 from theInternet: [URL: https:f/pubchem.ncbi.nlm.nih.gov/compound/24802108]; p. 2, see 2D structure.

(National Center for Biotechnology Information) "3-[2-[di(propan-2-yl)amino] ethyl)-1H-indol-4-yl) dihydrogen phosphate: Pubchem Cid 166138444" Pubchem entry (online), pp. 1-7. Dec. 20, 2022; Retrieved on Jul. 9, 2024 from the Internet: [URL: https:f/pubchemn. cbi.nlm.nih.gov/compound/166138444;]p. 2, see 2D structure.

Pubmed Compound Record for CID 84056101, 2-(2-Chloro-4-methoxy-1H-indol-3-yl)ethyanamine, U.S. National Library of Medicine, Oct. 20, 2014, pp. 1-7, (https://pubchem.ncbi.nlm.nih.gov/compound/84056101).

Pubmed Compound Record for CID 123606, Almotriptan, U.S. National Library of Medicine, Aug. 8, 2005 pp. 1-40, (https://pubchem.ncbi.nlm.nih.gov/compound/123606).

Pubmed Compound Record for CID 84058691, 1-(2-Chloro-4-methoxy-1H-indol-3-yl)propan-2-amine, U.S. National Library of Medicine, Oct. 20, 2014, pp. 1-7, (https://pubchem.ncbi.nlm.nih.gov/compound/84058691).

PCT International Search Report, PCT/US2131215 (Oct. 1, 2021).
PCT Written Opinion, PCT/US2131215 (Oct. 1, 2021).

Pubchem, Substance Record for SID 313512691, Available Date Jun. 11, 2016 [retrieved on Dec. 12, 2022] Retrieved from the Internet <URL:https://pubchem.ncbi.nlm.nih.gov/sustance/313512691>.

Pubchem, Substance Record for SID 471368824 Available Date Sep. 27, 2002 [retrieved on Feb. 1, 2023] Retrieved from the Internet <URL:https://pubchem.ncbi.nlm.nih.gov/sustance/471368824>.

Pubchem, Substance Record for SID 474211406 Available Date Dec. 15, 2002 [retrieved on Feb. 1, 2023] Retrieved from the Internet <URL:https://pubchem.ncbi.nlm.nih.gov/sustance/474211406>.

European Patent Office, Extended Search Report, EP Application Serial No. 21800237.6, Apr. 15, 2024.

Database Registry [Online] Chemical Abstract Service, Columbus, Ohio, US; Aug. 2, 2017 (Aug. 2, 2017), retrieved from STN Database accession No. 2107153-36-4.

Lyon R A et al: "Indolealkylamine analogs share 5-HT"2 binding characteristics with phenylalkylamine hallucinogens",European Journal of Pharmacology, Elsevier Science, NL, vol. 145, No. 3, Jan. 19, 1988, pp. 291-297.

Blough Bruce E et al: "Alpha-ethyltryptamines as dual dopamine serotonin releasers", Bioorganic & Medicinal Chemistry Letters, Elsevier, Amsterdam NL, vol. 24, No. 19, Jul. 29, 2014, pp. 4754-4758.

University of Zurich. Compositions and kits comprising N,N-dimethyltryptamine and harmine and their use in therapy. European Patent Application Serial No. EP20181489, filing date Jun. 24, 2020, receipt by WIPO Jul. 6, 2021.

Huang et al. Nose-to-brain delivery of drug nanocrystals by using Ca2+ responsive deacetylated gellan gum based in situ-nanogel. International Journal of Pharmaceuticals. 2020;S0378-5173(20)31167-4.

Mahalingam. Semisolid Dosages: Ointments, Creams, and Gels. in Pharmaceutical Manufacturing Handbook: Production and Processes. (Chapter 9, 267-312), Shayne C. Gad ed., John Wiley & Sons, Inc. 2008.

1 Japanese Patent Office, Official Action, JP 2022-567840, Nov. 28, 2024.

Abiero et al., "Four Novel Synthetic Tryptamine Analogs Induce Head-Twitch Responses and Increase 5-HTR2a in the Prefrontal Cortex in Mice." Biomol Ther (Seoul). Jan. 1, 2020; 28(1): 83-91.

Andersson et al., "Psychoactive substances as a last resort—a qualitative study of self-treatment of migraine and cluster headaches." Harm Reduct J. Sep. 5, 2017; 14(1):60. 11 pages.

Archer et al., "5-Methoxy-N, N-dimethyltryptamine-induced analgesia is blocked by alpha-adrenoceptor antagonists in rats." Br J Pharmacol. Oct. 1986;89(2):293-8. doi: 10.1111/j.1476-5381.1986.tb10259.x.

Baker et al., "Neurochemical and neuropharmacological investigation of N-cyanoethyltryptamine, a potential prodrug of tryptamine." Proc West Pharmacol Soc., 1987; 30: 307-11.

Baker et al., "Neuropharmacological and Neurochemical Properties of N-(2-Cyanoethyl)-2-Phenylethylamine, A Prodrug of 2-Phenylethylamine." Br J Pharmacol. Oct. 1987; 92(2): 243-55.

Banker, G. S., et al., "Modern Pharmaceutics." Third Edition, Revised, and Expanded, Marcel Dekker, Inc. (1996); pp. 451 and 596; 3 pages.

Barker, "Administration of N,N-dimethyltryptamine (DMT) in psychedelic therapeutics and research and the study of endogenous DMT." Psychopharmacology (Berl). Jun. 2022; 239(6): 1749-1763. Epub Jan. 22, 2022, with erratum, 16 pages.

Barker, "N, N-Dimethyltryptamine (DMT), an Endogenous Hallucinogen: Past, Present, and Future Research to Determine Its Role and Function." Front Neurosci. Aug. 6, 2018:12:536. doi: 10.3389/fnins.2018.00536. eCollection 2018. 17 pages.

Barsuglia et al., "Intensity of mystical experiences occasioned by 5-MeO-DMT and comparison with a prior psilocybin study." Front Psychol. Dec. 6, 2018: 9: 2459. doi: 10.3389/fpsyg.2018.02459. eCollection 2018. 6 pages.

Benneyworth et al., "Complex discriminative stimulus properties of (+)lysergic acid diethylamide (LSD) in C57Bl/6J mice." Psychopharmacology (2005) 179, 854-862.

Berge et al. "Pharmaceutical Salts" Jan. 1977, Journal of Pharmaceutical Sciences, 66(1):1-19.

Bergin, "Preliminary X-ray crystallographic study of some psychoactive indole bases." Acta Cryst. (1968). B24, 882, https://doi.org/10.1107/S0567740868003353, 1 page.

(56) References Cited

OTHER PUBLICATIONS

Bergin, "The structure of the catecholamines. II. The crystal structure of dopamine hydrochloride." Acta Crystallogr B Struct Crystallogr Cryst Chem. Nov. 15, 1968;24(11):1506-10. doi: 10.1107/s0567740868004553.

Bibi et al., "Use of Permeapad® for prediction of buccal absorption: A comparison to in vitro, ex vivo and in vivo method." Eur J Pharm Sci. Oct. 10, 2016:93:399-404. doi:10.1016/j.ejps.2016.08.041. Epub Aug. 24, 2016.

Brandt et al., "Analytical methods for psychoactive N,N-dialkylated tryptamines." Trends in Analytical Chemistry, vol. 29, No. 8, 2010, pp. 858-869.

Brandt et al., "Characterization of the synthesis of N,N-dimethyltryptamine by reductive amination using gas chromatography ion trap mass spectrometry." Drug Test Anal. Jul. 2010; 2(7): 330-8. doi: 10.1002/dta.142.

Brito-Da-Costa, et al., "Toxicokinetics and toxicodynamics of ayahuasca alkaloids N, N-dimethyltryptamine (DMT), harmine, harmaline and tetrahydroharmine: clinical and forensic impact." Pharmaceuticals (Basel). Oct. 23, 2020; 13(11): 334. doi: 10.3390/ph13110334. 36 pages.

Buchwald, Peter, "Soft drugs: design principles, success stories, and future perspectives." Expert Opin Drug Metab Toxicol. Aug. 2020; 16(8): 645-650. Epub Jun. 20, 2020.

Bugaenko et al., "Synthesis of indoles: recent advances." Russ. Chem. Rev., 2019, 88 (2)99-159, 62 pages.

Cameron et al., "A non-hallucinogenic psychedelic analogue with therapeutic potential." Nature. Jan. 2021;589(7842):474-479. doi: 10.1038/s41586-020-3008-z. Epub Dec. 9, 2020, and Reporting Summary, 24 pages.

Cameron et al., "Chronic, Intermittent Microdoses of the Psychedelic N, N-Dimethyltryptamine (DMT) Produce Positive Effects on Mood and Anxiety in Rodents." ACS Chemical Neuroscience, vol. 10, No. 7, Jul. 17, 2019 (Jul. 17, 2019), pp. 3261-3270.

Cameron et al., "Effects of N, N-Dimethyltryptamine on Rat Behaviors Relevant to Anxiety and Depression." ACS Chem Neurosci, Jul. 18, 2018; 9(7): 1582-1590. Epub Apr. 24, 2018.

Carhart-Harris et al., "The therapeutic potential of psychedelic drugs: past, present, and future." Neuropsychopharmacology (2017); 42(11): 2105-2113. doi: 10.1038/npp.2017.84. Epub Apr. 26, 2017.

Carhart-Harris et al., "Psilocybin for treatment-resistant depression: fMRI-measured brain mechanisms." Sci Rep. Oct. 13, 2017; 7(1): 13187. doi: 10.1038/s41598-017-13282-7. 11 pages.

Carter et al., "Modulating the rate and rhythmicity of perceptual rivalry alternations with the mixed 5-HT2A and 5-HT1A agonist psilocybin." Neuropsychopharmacology (2005); 30(6): 1154-1162. doi: 10.1038/sj.npp.1300621.

Carvalho et al., "Mucoadhesive drug delivery systems," BJPS, vol. 46, n. 1, Jan./Mar., 2010. 18 pages.

CAS Registry No. 1152718-19-8, Benzenemethanamine, N-[4-(1,1-dimethylethyl)cyclohexyl]-2,4-difluoro-α-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1, 1-dimethylpropyl)-, trans-(9CI), Jun. 1, 1990, 1 page.

CAS Registry No. 127456-44-4, 1H-Inden-5-ol, 6-[[[4-(1,1-dimethylethyl)cyclohexyl]amino]methyl]-2,3-dihydro-, trans-(9CI), Jun. 1, 1990, 1 page.

CAS Registry No. 127456-45-5, Phenol, 4-(1,1-dimethylethyl)-2-[[[4-(1,1-dimethylethyl)cyclohexyl]amino]methyl]-, trans-(9CI), Jun. 1, 1990, 1 page.

CAS Registry No. 127456-46-6, Phenol, 4-(1, 1-dimethylethyl)-2-[[[4-(1, 1-dimethylethyl)cyclohexyl]amino]methyl]-6-methyl-, hydrochloride, trans-(9CI), Jun. 1, 1990, 1 page.

CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.

CAS Registry No. 127456-56-8, Phenol, 4-chloro-2-[[[4-(1,1-dimethylethyl)cyclohexyl]amino]methyl]-, trans-(9CI), Jun. 1, 1990, 1 page.

CAS Registry No. 127456-57-9, Phenol, 2-[[[4-(1,1-dimethylethyl)cyclohexyl]amino]methyl]-4-fluoro-, trans-(9CI), Jun. 1, 1990, 2 pages.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1,1-dimethylpropyl)cyclohexyl]-2,3-difluoro-, Dec. 5, 2012, 1 page.

CAS Registry No. 1456349-79-3, Benzenemethanamine, 2,3-dichloro-N-[4-(1,1-dimethylpropyl)cyclohexyl]-, Oct. 6, 2013, 1 page.

CAS Registry No. 1458497-71-6, Benzenemethanamine, 2,4-dichloro-N-[4-(1,1-dimethylethyl)cyclohexyl]-α-methyl-, Oct. 15, 2013, 1 page.

CAS Registry No. 1459328-13-2, Phenol, 2-bromo-4-[[[4-(1,1-dimethylpropyl)cyclohexyl]amino]methyl]-, Oct. 16, 2013, 1 page.

CAS Registry No. 1490220-45-5, Benzenemethanamine, 2-bromo-5-chloro-N-[4-(1,1-dimethylpropyl)cyclohexyl]-, Dec. 8, 2013, 1 page.

CAS Registry No. 1515984-46-9, Benzamide, N-(4-aminocyclohexyl)-3-chloro-N,5-dimethyl-, Jan. 10, 2014, 1 page.

CAS Registry No. 1542027-51-9, Phenol, 3-chloro-2-[[[4-(1,1-dimethylpropyl)cyclohexyl]amino]methyl]-, Feb. 11, 2014, 1 page.

CAS Registry No. 1624268-56-9, Benzamide, 4-[[[4-(1,1-dimethylethyl)cyclohexyl]amino]methyl]-N-methyl-, Sep. 22, 2014, 1 page.

CAS Registry No. 1712122-27-4, Benzenemethanamine, 5-chloro-N-[4-(1,1-dimethylpropyl)cyclohexyl]-2-fluoro-, May 25, 2015, 1 page.

CAS Registry No. 1772618-27-5, Phenol, 3-[[[4-(1,1-dimethylpropyl)cyclohexyl]amino]methyl]-5-fluoro-, Jun. 3, 2015, 1 page.

CAS Registry No. 1775706-37-0, Phenol, 2-chloro-6-[[[4-(1,1-dimethylpropyl)cyclohexyl]amino]methyl]-, Jun. 8, 2015, 1 page.

CAS Registry No. 1858436-76-6, Bicyclo[3.1.0]hexan-2-amine, N-[(3-chloro-5-methylphenyl)methyl]-, Feb. 3, 2016, 1 page.

CAS Registry No. 1931388-10-1, Benzenemethanamine, 2,5-dichloro-N-[4-(1,1-dimethylpropyl)cyclohexyl]-, Jun. 14, 2016, 1 page.

CAS Registry No. 1939264-55-7, Phenol, 4-[[[4-(1,1-dimethylpropyl)cyclohexyl]amino]methyl]-2-fluoro-, Jun. 26, 2016, 1 page.

CAS Registry No. 1939792-99-0, Benzenemethanamine, 5-bromo-2-chloro-N-[4-(1,1-dimethylpropyl)cyclohexyl]-, Jun. 27, 2016, 1 page.

CAS Registry No. 1962333-15-8, Benzenemethanamine, N-[4-(1,1-dimethylpropyl)cyclohexyl]-5-fluoro-2-methyl-, Jul. 29, 2016, 1 page.

CAS Registry No. 2032268-58-7, Cyclohexanecarboxylic acid, 4-[[(3-chloro-5-methylphenyl)methyl]amino]-, Nov. 15, 2016, 1 page.

CAS Registry No. 2199998-08-6, Cyclohexanecarboxylic acid, 2-[[(3-chloro-5-methylphenyl)methyl]amino]-1-methyl-, Mar. 27, 2018, 1 page.

CAS Registry No. 2202151-69-5, Cyclohexanecarboxylic acid, 3-[[(3-chloro-5-methylphenyl)methyl]amino]-, Mar. 30, 2018, 1 page.

CAS Registry No. 2322790-81-6, Benzenemethanamine, N-[4-(1,1-dimethylethyl)cyclohexyl]-3-(trifluoromethyl)-, Jun. 2, 2019, 1 page.

CAS Registry No. 2419600-39-6, Benzenemethanamine, 3-chloro-N-[4-(1,1-dimethylpropyl)cyclohexyl]-5-methyl-, Jun. 5, 2020, 1 page.

CAS Registry No. 415970-94-4, Benzenemethanamine, N-[4-(1,1-dimethylethyl)cyclohexyl]-3,5-dimethoxy-, May 15, 2002, 1 page.

CAS Registry No. 744981-83-7, Phenol, 2,6-dibromo-4-[[[4-(1,1-dimethylethyl)cyclohexyl]amino]methyl]-, Sep. 15, 2004, 1 page.

(56) References Cited

OTHER PUBLICATIONS

CAS Registry No. 793633-39-3, Phenol, 4-(1,1-dimethylethyl)-2-[[[trans-4-(1,1-dimethylethyl)cyclohexyl]amino]methyl]-6-methyl-, Dec. 6, 2004, 1 page.

Cayman Chemical "Safety Data Sheet Acc. to OSHA HCS", N,N-DMT (Succinate), CAS No. 2853570-32-6, Cayman Chemical: 1-7, Revised Feb. 15, 2024.

Cayman Chemical, "Safety Data Sheet", Caymanchem.com, Apr. 21, 2021, [online] available at: https://cdn.caymanchem.com/cdn/msds/33586m.pdf. 6 printed pages.

Cayman Chemical, product information for Item No. 33586, "N,N-DMT (succinate)." Apr. 26, 2021, 1 page.

Chadeayne, Andrew R et al., "The Crystal Structure of 4-AcO-DMT Fumarate." Psychedelic Science Review, Science Review Team, Mar. 25, 2019, online at: https://psychedelicreview.com/the-crystal-structure-of-4-aco-dmt-fumarate/, 11 pages.

Chegaev, et al., "NO-donor melatonin derivatives: synthesis and in vitro pharmacological characterization", J Pineal Res. Apr. 2007; 42(4): 371-85.

Chen, et al., "Structure-activity relationships in a series of 5-[(2,5-dihydroxybenzyl) amino] salicylate inhibitors of EGF-receptor-associated tyrosine kinase: importance of additional hydrophobic aromatic interactions." J Med Chem. Mar. 18, 1994;37(6):845-59. doi: 10.1021/jm00032a020.

ClinicalTrials.gov, "Effects of Dimethyltryptamine in Healthy Subjects (DMT)", Apr. 20, 2020, 9 pages. Retrieved on Jun. 24, 2022 from https://clinicaltrials.gov/ct2/show/NCT04353024.

Cocchi et al., "Novel Psychoactive Phenethylamines: Impact on Genetic Material." Int J Mol Sci. Dec. 17, 2020; 21(24): 9616. doi: 10.3390/ijms21249616. 17 pages.

Corne et al., "A possible correlation between drug-induced hallucinations in man and a behavioural response in mice", Psychopharmacologia (Berl.) (1967); 11: 65-78. doi: 10.1007/BF00401509.

Cozzi, Nicholas V. et al., "Synthesis and characterization of high-purity N,N-dimethyltryptamine hemifumarate for human clinical trials." Drug Test Anal. Oct. 2020; 12(10): 1483-1493. doi: 10.1002/dta.2889. Epub Jul. 14, 2020.

Daiber et al., "Organic Nitrate Therapy, Nitrate Tolerance, and Nitrate-Induced Endothelial Dysfunction: Emphasis on Redox Biology and Oxidative Stress." Antioxid Redox Signal. Oct. 10, 2015;23(11):899-942.).

Dakic et al., "Short term changes in the proteome of human cerebral organoids induced by 5-MeO-DMT." Sci Rep. Oct. 9, 2017;7(1):12863. doi: 10.1038/s41598-017-12779-5. 13 pages.

Dalgleish, T., et al., "Transdiagnostic Approaches to Mental Health Problems: Current Status and Future Directions." Journal of Consulting and Clinical Psychology, 2020, vol. 88, No. 3, 179-195.

Davis et al., "5-methoxy-N, N-dimethyltryptamine (5-MeO-DMT) used in a naturalistic group setting is associated with unintended improvements in depression and anxiety." Am J Drug Alcohol Abuse. 2019; 45(2): 161-169. doi: 10.1080/00952990.2018. 1545024. Epub Mar. 1, 2019. 10 pages.

Davis, et al., "The epidemiology of 5-methoxy-N, N-dimethyltryptamine (5-MeO-DMT) use: Benefits, consequences, patterns of use, subjective effects, and reasons for consumption." J Psychopharmacol, Jul. 2018. vol. 2, Issue 7, Epub Apr. 30, 2018. 14 pages.

De Barros et al., "Synthesis of 25X-BOMes and 25X-NBOHs (X = H, I, Br) for pharmacological studies and as reference standards for forensic purposes." Tetrahedron Letters 66 (2021) 152804, 4 pages.

Declaration of Majed Fawaz under 37 C.F.R. § 1.130, in U.S. Appl. No. 17/824,861, dated Jun. 2024, 2 pages.

Dimoitou, "Nasal spray" #3 Posted : Jun. 27, 2014 6:58:57 pm DMT-Nexus, Jun. 27, 2014, https://forum.dmt-nexus.me/threads/nasal-spray.343226/. 5 pages.

Du, M., "An Overview on Transmucosal Permeability and Formulation." J Develop Drugs. 13:227, (2024), 2 pages.

Dunlap et al., "Identification of psychoplastogenic N, N-dimethylaminoisotryptamine (isoDMT) analogues through structure-activity relationship studies." J Med Chem Feb. 13, 2020; 63(3): 1142-1155. Epub Jan. 24, 2020. 14 pages.

Dunlap, Lee, E. et al., Reaction of N, N-Dimethyltryptamine with Dichloromethane Under Common Experimental Conditions, ACS Omega, 2018, 3, 4968-4973.

Durham and Russo, "Regulation of calcitonin gene-related peptide secretion by a serotonergic antimigraine drug." J Neurosci. May 1, 1999; 19(9): 3423-9. doi: 10.1523/JNEUROSCI.19-09-03423.1999.

Extended European Search Report for EP Application No. 22796577. 9, dated Mar. 10, 2025, 10 pages.

Extended European Search Report for EP Application No. 22812068. 9, dated Mar. 28, 2025, 13 pages.

Falkenberg et al., "The crystal and molecular structure of (N,N)-dimethyltryptamine." Acta Crystallogr., Sect B28, 3075-3083, Mar. 9, 1972, 9 pages.

Gaujac et al. "Determination of N,N-dimethyltryptamine in beverages consumed in religious practices by headspace solid-phase microextraction followed by gas chromatography ion trap mass spectrometry," Talanta. Mar. 15, 2013: 106:394-8. doi: 10.1016/j.talanta.2013.01.017. Epub Feb. 1, 2013.

Gaujac et al., "Investigations into the polymorphic properties of N, N-dimethyltryptamine by X-ray diffraction and differential scanning calorimetry," Microchemical Journal 110, Mar. 2, 2013, 12 pages.

Glatfelter G, et al., "Synthesis, Structural Characterization, and Pharmacological Activity of Novel Quaternary Salts of 4-Substituted Tryptamines", ACS Omega, Jul. 2022, vol. 7(28), pp. 24888-24894.

Glennon et al., "Hallucinogens as discriminative stimuli: A comparison of 4-OMe and 5-OMe DMT with their methylthio counterparts", Life Science, Pergamon Press, Oxford, GB, vol. 30, No. 5, Feb. 1, 1982 (Feb. 1, 1982), pp. 465-467, XP023723306, ISSN: 0024-3205, DOI: 10.1016/0024-3205(82)90463-5 [retrieved on Feb. 1, 1982].

Glennon et al., "Influence of amine substituents on 5-HT2A versus 5-HT2C binding of phenylalkyl-and indolylalkylamines." J Med Chem. Jun. 24, 1994; 37(13): 1929-35. doi: 10.1021/jm00039a004.

Glennon et al., "Synthesis and evaluation of a novel series of N,N-dimethylisotryptamines", J Med Chem. Jan. 1984; 27(1): 41-5.

Gonzalez-Maeso et al., "Hallucinogens Recruit Specific Cortical 5-HT2A Receptor-Mediated Signaling Pathways to Affect Behavior," Neuron, Feb. 2007, 53, 439-452.

Gribble, "Recent developments in indole ring synthesis-methodology and applications", Journal of the Chemical Society, Perkin Transactions, 2000, pp. 1045-1075.

Griffiths et al., "Psilocybin produces substantial and sustained decreases in depression and anxiety in patients with life-threatening cancer: a randomized double-blind trial", Journal of Psychopharmacology (2016); 30: 1181-1197. doi: 10.1177/0269881116675513.

Grundke et al., "Photochemical α-Aminonitrile Synthesis Using Zn-Phthalocyanines as Near-Infrared Photocatalysts", J Org Chem. May 6, 2022; 87(9): 5630-5642, with supporting info. Epub Apr. 14, 2022. 60 pages.

Gurevich and Gurevich, "GPCR Signaling Regulation: The Role of GRKs and Arrestins", Front Pharmacol. Feb. 19, 2019: 10: 125. eCollection 2019, 11 pages.

Halberstadt, A. L., "Recent Advances in the Neuropsychopharmacology of Serotonergic Hallucinogens." Behav Brain Res. Jan. 15, 2015: 277: 99-120. doi: 10.1016/j.bbr.2014.07.016. Epub Jul. 15, 2014.

Halberstadt et al., "Differential contributions of serotonin receptors to the behavioral effects of indoleamine hallucinogens in mice", J Psychopharmacol. Nov. 2011; 25(11): 1548-61. Epub Dec. 8, 2010.

Hamada et al., "Water-soluble prodrugs of dipeptide HIV protease inhibitors based on O→N intramolecular acyl migration: Design, synthesis and kinetic study" Bioorg Med Chem. Jan. 2, 2004;12(1):159-70. doi: 10.1016/j.bmc.2003.10.026.

Hansen et al., "Synthesis and pharmacological evaluation of N-benzyl substituted 4-bromo-2,5-dimethoxyphenethylamines as 5-HT2A/2C partial agonists." Bioorganic & Medicinal Chemistry 23 (2015), 3933-3937.

(56) References Cited

OTHER PUBLICATIONS

Hansen et al., "Synthesis and Structure-Activity Relationships of N-Benzyl Phenethylamines as 5-HT2A/2C Agonists." ACS Chem Neurosci. Mar. 19, 2014;5(3):243-9. doi: 10.1021/cn400216u. Epub Jan. 15, 2014.
Harriott et al., "Animal models of migraine and experimental techniques used to examine trigeminal sensory processing", J Headache Pain. Aug. 29, 2019; 20(1): 91. 15 pages.
Hart et al., "Melting Point Determination, Melting Range", Adapted from Organic Chemistry: A Short course, 13th ed. Houghton-Mifflin, Boston, 2012, available at: https://chemistry.sites.clemson.edu/organic/Labs/2270Docs/MeltingPoint.pdf, 4 pages.
Hasegawa et al., "A Novel Methodology for Preparing 5-chloro- and 5-bromo-tryptamines and tryptophans, and its Application to the Synthesis of (+/−)-bromochelonin BI." (1999), Heterocycles, vol. 51, No. 12, pp. 2815-2821.
Holze et al. "Distinct acute effects of LSD, MDMA, and Damphetamine in healthy subjects." Neuropsychopharmacology. Feb. 2020;45(3):462-471.
Humphrey et al., "Practical methodologies for the synthesis of indoles", Chem Rev. Jul. 2006; 106(7): 2875-911, 37 pages.
Huttunen, et al., "Prodrugs-from Serendipity to Rational Design", Pharmacological Reviews, vol. 63, No. 3, Sep. 2011, pp. 750-771.
International Preliminary Report on Patentability for International Application No. PCT/US2022/026396, mailed Nov. 9, 2023, 8 pages.
International Preliminary Report on Patentability for International Application No. PCT/US2022/030912, mailed Dec. 7, 2023, 10 pages.
International Preliminary Report on Patentability for International Application No. PCT/US2022/032918, mailed Dec. 21, 2023, 7 pages.
International Preliminary Report on Patentability for International Application No. PCT/US2022/045336, mailed Apr. 11, 2024, 7 pages.
International Preliminary Report on Patentability for International Application No. PCT/US2022/047520, mailed May 10, 2024, 8 pages.
International Preliminary Report on Patentability for International Application No. PCT/US2023/073574, mailed Mar. 20, 2025, 9 pages.
International Search Report and Written Opinion for International Application No. PCT/US2022/026396, mailed Jul. 28, 2022, 10 pages.
International Search Report and Written Opinion for International Application No. PCT/US2022/030912, mailed Oct. 5, 2022, 20 pages.
International Search Report and Written Opinion for International Application No. PCT/US2022/032918, mailed Oct. 12, 2022, 10 pages.
International Search Report and Written Opinion for International Application No. PCT/US2022/045336, mailed Jan. 13, 2023, 14 pages.
International Search Report and Written Opinion for International Application No. PCT/US2022/047520, mailed Mar. 1, 2023, 11 pages.
International Search Report and Written Opinion for International Application No. PCT/US2022/082465, mailed Jun. 6, 2023, 11 pages.
International Search Report and Written Opinion for International Application No. PCT/US2023/073574, mailed Feb. 16, 2024, 13 pages.
International Search Report and Written Opinion for International Application No. PCT/US2023/077879, mailed Apr. 4, 2024, 11 pages.
International Search Report and Written Opinion for International Application No. PCT/US2023/082080, mailed Apr. 4, 2024, 8 pages.
International Search Report and Written Opinion for International Application No. PCT/US2023/084319, mailed May 20, 2024, 13 pages.
International Search Report and Written Opinion for International Application No. PCT/US2024/026797, mailed Sep. 6, 2024, 10 pages.
International Search Report and Written Opinion for International Application No. PCT/US2024/036639, mailed Sep. 23, 2024, 11 pages.
International Search Report and Written Opinion for International Application No. PCT/US2024/038804, mailed Dec. 17, 2024, 14 pages.
International Search Report and Written Opinion for International Application No. PCT/US2024/039503, mailed Nov. 5, 2024, 17 pages.
International Search Report and Written Opinion for International Application No. PCT/US2024/045494, mailed Nov. 15, 2024, 11 pages.
International Search Report and Written Opinion for International Application No. PCT/US2024/049678, mailed Jan. 21, 2025, 9 pages.
International Search Report and Written Opinion for International Application No. PCT/US2025/014571, mailed Mar. 21, 2025, 15 pages.
International Search Report and Written Opinion for PCT Application No. PCT/US2024/061478 mailed Apr. 23, 2025, 10 pages.
Invitation to Pay Additional Fees for International Application No. PCT/US2022/030912, mailed Jul. 28, 2022, 8 pages.
Invitation to Pay Additional Fees for International Application No. PCT/US2022/032918, mailed Aug. 12, 2022, 2 pages.
Invitation to Pay Additional Fees for International Application No. PCT/US2022/082465, mailed Mar. 16, 2023, 3 pages.
Invitation to Pay Additional Fees for International Application No. PCT/US2023/073574, mailed Nov. 6, 2023, 2 pages.
Invitation to Pay Additional Fees for International Application No. PCT/US2024/026797, mailed Jun. 25, 2024, 2 pages.
Invitation to Pay Additional Fees for International Application No. PCT/US2024/038804, mailed Sep. 23, 2024, 3 pages.
Invitation to Pay Additional Fees for International Application No. PCT/US2024/039503, mailed Sep. 10, 2024, 2 pages.
Invitation to Pay Additional Fees for International Application No. PCT/US2024/061478, mailed Feb. 25, 2025, 2 pages.
Invitation to Pay Additional Fees for International Application No. PCT/US22/47520, mailed Jan. 3, 2023, 2 pages.
Kaminska et al., "25C-NBOMe short characterization", Forensic Toxicology, 2020, pp. 490-495.
Klein et al., "Toward selective drug development for the human 5-hydroxytryptamine 1E receptor: a comparison of 5-hydroxytryptamine 1E and 1F receptor structure-affinity relationships", J Pharmacol Exp Ther. Jun. 2011; 337(3): 860-7. Epub Mar. 21, 2011.
Kline et al, "Structure-activity relationships in potentially hallucinogenic N, N-dialkyltryptamines substituted in the benzene moiety." J Med Chem. Aug. 1982; 25(8):908-13. doi: 10.1021/jm00350a005.
Kraehenmann et al., "Dreamlike effects of LSD on waking imagery in humans depend on serotonin 2A receptor activation", Psychopharmacology (Berl) (2017); 234: 2031-2046. doi: 10.1007/s00213-017-4610-0. Epub Apr. 7, 2017.
Kraehenmann et al., "LSD Increases Primary Process Thinking via Serotonin 2A Receptor Activation", Frontiers in Pharmacology (2017); 8: 814; 9 pages. doi: 10.3389/fphar.2017.00814.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Kucklander, et al., "Darstellung und Oxidation von 2-(2, 5-Dihydroxyphenyl)-ethylamin-Derivaten, II/Synthesis and Oxidation of 2-(2, 5-Dihydroxyphenyl)-ethylamine Derivatives, II", Zeitschrift für Naturforschung B, 1987, pp. 1567-1577 (with English abstract). 12 pages.
Li et al., "Treatment of breast and lung cancer cells with a N-7 benzyl guanosine monophosphate tryptamine phosphoramidate

(56) References Cited

OTHER PUBLICATIONS pronucleotide (4Ei-1) results in chemosensitization to gemcitabine and induced eIF4E proteasomal degradation." Mol Pharm., Feb. 2013, pp. 523-531.

Lima da Cruz et al., "Corrigendum: A Single Dose of 5-MeO-DMT Stimulates Cell Proliferation, Neuronal Survivability, Morphological and Functional Changes in Adult Mice Ventral Dentate Gyrus." Front Mol Neurosci. Sep. 4, 2018;11:312. doi: 10.3389/fnmol.2018.00312. eCollection 2018. 11 pages.

Lyon et al., "3, 4-Methylenedioxymethamphetamine (MDMA): stereoselective interactions at brain $5-HT_1$ and $5-HT_2$ receptors." Psychopharmacology (1986); 88: 525-526. doi: 10.1007/BF00178519.

Madsen et al., "Psilocybin-induced reduction in chronic cluster headache attack frequency correlates with changes in hypothalamic functional connectivity", medRxiv. Jul. 10, 2022: 2022-07.

Madsen et al., "Psychedelic effects of psilocybin correlate with serotonin 2A receptor occupancy and plasma psilocin levels," Neuropsychopharmacology (2019) 44: 1328-1334.

Malaca, S., et al., "Toxicology and Analysis of Psychoactive Tryptamines." Int J Mol Sci. Dec. 4, 2020; 21(23): 9279. doi: 10.3390/ijms21239279. 30 pages.

McBride, "Bufotenine: Toward an Understanding of Possible Psychoactive Mechanisms", Journal of Psychoactive Drugs, Jul.-Sep. 2000, pp. 321-331.

McClure-Begley and Roth, "The promises and perils of psychedelic pharmacology for psychiatry", Nat Rev Drug Discov. Jun. 2022; 21(6): 463-473. Epub Mar. 17, 2022.

Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.

Milne et al., "Metabolic engineering of *Saccharomyces cerevisiae* for the de novo production of psilocybin and related tryptamine derivatives." Metab Eng. Jul. 2020:60:25-36. doi: 10.1016/j.ymben.2019.12.007. Epub Mar. 26, 2020.

Mithoefer et al., "The safety and efficacy of {+/−}3,4-methylenedioxymethamphetamine-assisted psychotherapy in subjects with chronic, treatment-resistant posttraumatic stress disorder: the first randomized controlled pilot study." J Psychopharmacol. Apr. 2011; 25(4): 439-52. doi: 10.1177/0269881110378371. Epub Jul. 19, 2010.

Mokler D J et al: "The 5HT"2 antagonist pirenperone reverses disruption of FR-40 by hallucinogenic drugs." Pharmacology Biochemistry and Behavior, Elsevier, US, vol. 22, No. 5, May 1, 1985 (May 1, 1985), pp. 677-682, XP023807793, ISSN: 0091-3057, DOI: 10.1016/0091-3057(85)90512-X [retrieved on May 1, 1985].

National Center for Biotechnology Information (2023). PubChem Substance Record for SID 309311543, SID 309311543, Source: Aurora Fine Chemicals LLC. Modified Jan. 30, 2016, retrieved from https://pubchem.ncbi.nlm.nih.gov/substance/309311543, 5 pages.

National Center for Biotechnology Information. PubChem Compound Summary for CID 15274381, 2-(7-Bromo-1H-indol-3-yl)ethan-1-amine. https://pubchem.ncbi.nlm.nih.gov/compound/2-_7-Bromo-1H-indol-3-yl_ethan-1-amine, Create date Feb. 9, 2007, Modify date Jan. 25, 2025, 14 pages.

National Center for Biotechnology Information. PubChem Compound Summary for CID 156821129, [3-[2-(Dimethylamino)ethyl]-4-hydroxyindol-1-yl]methylphosphonic acid. https://pubchem.ncbi.nlm.nih.gov/compound/156821129, created Nov. 20, 2021, Modify date Aug. 23, 2024, 10 pages.

National Center for Biotechnology Information. PubChem Compound Summary for CID 6089, Dimethyltryptamine. https://pubchem.ncbi.nlm.nih.gov/compound/Dimethyltryptamine. Create date: Mar. 26, 2005 (Mar. 26, 2005), 6 pages.

National Center for Biotechnology Information. PubChem Compound Summary for CID 10624, Psilocybin. https://pubchem.ncbi.nlm.nih.gov/compound/Psilocybin. Create date Mar. 3, 2005, Accessed May 5, 2025. 62 pages.

National Center for Biotechnology Information. PubChem Compound Summary for CID 88309097, [1-[[2-(1H-indol-3-yl)-1-(2-methylphenyl)ethyl]amino]-2-oxoethyl] carbamate. https://pubchem.ncbi.nlm.nih.gov/compound/88309097, Created date Feb. 12, 2015, Modified date Nov. 9, 2024, 8 pages.

National Center for Biotechnology Information. PubChem Substance Record for SID 310331158, SID 310331158, Source: Aurora Fine Chemicals LLC. https://pubchem.ncbi.nlm.nih.gov/substance/310331158, Modify Date: Feb. 15, 2015, 4 pages.

National Center for Biotechnology Information. PubChem Substance Record for SID 369863280, SID 369863280, Source: Ambinter. https://pubchem.ncbi.nlm.nih.gov/substance/369863280. Deposit date May 25, 2018, Modify Date: May 25, 2018, 5 pages.

National Center for Biotechnology Information. PubChem Substance Record for SID 433987242, N,N-dimethyltryptamine, Source: BioCyc. https://pubchem.ncbi.nlm.nih.gov/substance/433987242, Available Date: Sep. 28, 2020 [retrieved on Mar. 2, 2023, 7 pages.

National Center for Biotechnology Information. PubChem Substance Record for SID 627609, 2-(1H-indol-3-yl)ethanamine, Source: NIAID ChemDB. https://pubchem.ncbi.nlm.nih.gov/substance/627609, Modify Date: Jan. 21, 2015 [retrieved on Mar. 2, 2023]. 8 pages.

Nichols, D. E., "Psychedelics." Pharmacol Rev. Apr. 2016;68(2):264-355.

Nichols, "Hallucinogens." Pharmacol Ther. Feb. 2004; 101(2):131-81.

Nichols, "Structure-Activity Relationships of Phenethylamine Hallucinogens." J Pharm Sci. Aug. 1981; 70(8): 839-49.

Oliver et al., "Beta-blockers: Historical Perspective and Mechanisms of Action." Rev Esp Cardiol (Engl Ed). Oct. 2019; 72(10): 853-862).

Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.

Ott, J., "Pharmañopo—Psychonautics: Human intranasal, sublingual, intrarectal, pulmonary and oral pharmacology of bufotenine." J Psychoactive Drugs. Jul.-Sep. 2001; 33(3): 273-81.

Ott, J., "Pharmepena-psychonautics: human intranasal, sublingual and oral pharmacology of 5-methoxy-N, N-dimethyl-tryptamine." J Psychoactive Drugs. Oct.-Dec. 2001;33(4):403-7.

Pandy-Szekeres et al., "GPCRdb in 2023: state-specific structure models using AlphaFold2 and new ligand resources", Nucleic Acids Res. Jan. 6, 2023; 51(D1): D395-D402. 8 pages.

Pandy-Szekeres et al., "The G Protein Database, GproteinDb." Nucleic Acids Res. Jan. 7, 2022; 50(D1): D518-D525.

Perez Custodio et al., "25B-NBOMe, a novel N-2-methoxybenzyl-phenethylamine (NBOMe) derivative, may induce rewarding and reinforcing effects via a dopaminergic mechanism: evidence of abuse potential." Addict Biol. Nov. 2020; 25(6):e12850. doi: 10.1111/adb.12850. Epub Nov. 20, 2019, 12 pages.

Pokorny et al., "Modulatory effect of the 5-HT1A agonist buspirone and the mixed non-hallucinogenic 5-HT1A/2A agonist ergotamine on psilocybin-induced psychedelic experience." Eur Neuropsychopharmacol. Apr. 2016; 26(4):756-66. doi: 10.1016/j.euroneuro.2016.01.005. Epub Jan. 22, 2016.

Pottie et al., "Identification of psychedelic new psychoactive substances (NPS) showing biased agonism at the 5-HT2AR through simultaneous use of β-arrestin 2 and miniGαq bioassays", Biochem Pharmacol. Dec. 2020: 182: 114251. Epub Sep. 28, 2020. 37 pages.

Preller et al., "Effects of serotonin 2A/1A receptor stimulation on social exclusion processing," PNAS, May 3, 2016, vol. 113, No. 18, 5119-5124.

Preller et al., "Role of the 5-HT2A Receptor in Self- and Other-Initiated Social Interaction in Lysergic Acid Diethylamide-Induced States: A Pharmacological fMRI Study", Journal of Neuroscience (Apr. 2018); 38(14): 3603-3611. doi: 10.1523/JNEUROSCI.1939-17.2018. Epub Mar. 19, 2018.

Preller et al., "The fabric of meaning and subjective effects in LSD-induced states depend on serotonin 2A receptor activation", Current Biology (2017); 27(3): 451-457. doi: 10.1016/j.cub.2016.12.030. Epub Jan. 26, 2017.

(56) References Cited

OTHER PUBLICATIONS

Prescribing information for BREVIBLOC (Esmolol Hydrochloride): www.baxterpi.com/pi-pdf/Brevibloc_PI.pdf), Initial U.S. approval: 1986, revised Apr. 2018, 19 pages.
Puledda et al., "An update on migraine: current understanding and future directions," J Neurol (2017) 264:2031-2039.
Puri et al., "Thiolation of Biopolymers for Developing Drug Delivery Systems with Enhanced Mechanical and Mucoadhesive Properties: A Review." Polymers (Basel). Aug. 11, 2020;12(8): 1803. doi: 10.3390/polym12081803. 27 pages.
Ray, T., "Psychedelics and the Human Receptorome," PLoS ONE (2010) 5(2): e9019, 17 pages.
Response to Office Action, European Patent Office, EP Application Serial No. 21800237.6, Oct. 30, 2024. 13 pages.
Riba, et al., "Metabolism and urinary disposition of N,N-dimethyltryptamine after oral and smoked administration: a comparative study", Drug Test Anal. May 2015;7(5):401-6. Epub Jul. 28, 2014.
Roth et al., "High-affinity Agonist Binding Is Not Sufficient for Agonist Efficacy at 5-Hydroxytryptamine2A Receptors: Evidence in Favor of a Modified Ternary Complex Model", The Journal of Pharmacology and Experimental Therapeautics, 1997, vol. 280, No. 2, pp. 576-583.
Ruiz et al, "Routes of Drug Administration: Dosage, Design, and Pharmacotherapy Success", In book: ADME Processes in Pharmaceutical Sciences, Chapter 6, Jan. 2018, DOI:10.1007/978-3-319-99593-9_6, 44 pages.
Santos-Longhurst, A, "How Long Does DMT Last?" Healthline. com, Nov. 24, 2019, [online] retrieved on Jun. 24, 2022 from https://www.healthline.com/health/how-long-does-dmt-last, 12 pages.
Sargent et al., "Radiohalogen-Labeled Imaging Agents. 3. Compounds for Measurement of Brain Blood Flow by Emission Tomography," Journal of Medicinal Chemistry (1984), 27(8), 1071-1077.
Satheesh Madhav et al., "Orotransmucosal drug delivery systems: A review." J Control Release. Nov. 16, 2009; 140(1): 2-11. doi:10.1016/j.jconrel.2009.07.016. Epub Aug. 6, 2009.
Schifano et al., "New psychoactive substances (NPS) and serotonin syndrome onset: A systematic review", Exp Neurol. May 2021: 339: 113638. Epub Feb. 8, 2021. 29 pages.
Schindler et al., "Exploratory Controlled Study of the Migraine-Suppressing Effects of Psilocybin", Neurotherapeutics, Jan. 2021; 18(1): 534-543. Epub Nov. 12, 2020. 10 pages.
Schlag et al., "Adverse effects of psychedelics: From anecdotes and misinformation to systematic science." J Psychopharmacol. Mar. 2022; 36(3): 258-272.
Shen et al., "Psychedelic 5-Methoxy-N,N-dimethyltryptamine: Metabolism, Pharmacokinetics, Drug Interactions, and Pharmacological Actions", Curr Drug Metab., Oct. 2010; 11(8): 659-666.
Shen L, et al., "Bufotenines-loaded liposome exerts anti-inflammatory, analgesic effects and reduce gastrointestinal toxicity through altering lipid and bufotenines metabolism", Biomed Pharmacother, Sep. 2022, vol. 153, pp. 1-12.
Sherwood et al., "Synthesis and characterization of 5-MeO-DMT succinate for clinical use", ACS Omega (2020); 5(49): 32067-32075. doi: 10.1021/acsomega.0c05099.
Sigma, Succinic acid—Butanedioic acid, CAS No. 110-15-6, Merck KGaA, 2023, 4 pages.
Sizemore et al., "Serotonergic Modulation Across Sensory Modalities." J Neurophysiol. Jun. 1, 2020;123(6):2406-2425. doi: 10.1152/jn.00034.2020. Epub May 13, 2020.
Sizemore, T.R, and Dacks, A.M., "Circadian Clocks: Mosquitoes Master the Dark Side of the Room", Curr Biol. Aug. 17, 2020; 30(16): R932-R934. 3 pages.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Strassman, "N-dimethyltryptamine in humans: II. Subjective effects and preliminary results of a new rating scale", Arch Gen Psychiatry. Feb. 1994; 51(2): 98-108.
Terry, Alvin V., "Drugs that target serotonergic receptors." Cognitive Enhancing Drugs, pp. 79-80, Ed. J. Buccafusco, Birkhauser, 2004, 2 pages.
Thoai, et al., "Design and Synthesis of Sustain-Acting Melatonin Prodrugs", Sep. 12, 2013 (Sep. 12, 2013), Journal of Chemistry, vol. 2013, Issue 1, pp. 1-6.
Timmermann, Christopher et al. "Neural correlates of the DMT experience assessed with multivariate EEG." Sci Rep. Nov. 19, 2019;9(1):16324. 13 pages.
Tirapegui et al., "Synthesis of N-(halogenated) benzyl analogs of superpotent serotonin ligands," J. Chil. Chem. Soc., (2014) 59, No. 3, pp. 2625-2627.
Titeler et al., "Radioligand binding evidence implicates the brain 5 HT2 receptor as a site of action for LSD and phenylisopropylamine hallucinogens", Psychopharmacology (Berl). (1988); 94: 213-216. doi: 10.1007/BF00176847.
Tomaszewski et al., "Benzofuran Bioisosteres of Hallucinogenic Tryptamines," J. Med. Chem., 1992, 35, pp. 2061-2064.
Uthaug et al., "A single inhalation of vapor from dried toad secretion containing 5-methoxy-N, N-dimethyltryptamine (5-MeO-DMT) in a naturalistic setting is related to sustained enhancement of satisfaction with life, mindfulness-related capacities, and a decrement of psychopathological symptoms," Psychopharmacology (2019) 236:2653-2666.
Uthaug et al., "Prospective examination of synthetic 5-methoxy-N,N-dimethyltryptamine inhalation: effects on salivary IL-6, cortisol levels, affect, and non-judgment," Psychopharmacology (2020) 237:773-785.
Valle et al., "Inhibition of alpha oscillations through serotonin-2A receptor activation underlies the visual effects of ayahuasca in humans", European Neuropsychopharmacology (2016); 26(7): 1161-1175. doi: 10.1016/j.euroneuro.2016.03.012. Epub Mar. 25, 2016.
Viracocha, "The DMT Handbook." Dec. 2008, URL:https://catbull.com/alamut/Bibliothek/DMT_Handbook.pdf. 31 pages.
Vollenweider et al., "Psilocybin induces schizophrenia-like psychosis in humans via a serotonin-2 agonist action", Neuroreport (1998); 9(17): 3897-3902. doi: 10.1097/00001756-199812010-00024.
Vollenweider et al., "Psychedelic drugs: neurobiology and potential for treatment of psychiatric disorders", Nature Reviews Neuroscience (2020); 21(11): 611-624. doi: 10.1038/s41583-020-0367-2. Epub Sep. 14, 2020.
Wang et al., "Anti-inflammatory and analgesic actions of bufotenine through inhibiting lipid metabolism pathway," Biomedicine & Pharmacotherapy (2021) 140: 111749, 11 pages.
Wey et al., "Structure-based design, synthesis, and biological evaluation of indomethacin derivatives as cyclooxygenase-2 inhibiting nitric oxide donors." J Med Chem. Dec. 13, 2007;50(25):6367-82. doi: 10.1021/jm0611861. Epub Nov. 10, 2007.
Wikipedia, "Perfusion", Dec. 29, 2020 (Dec. 29, 2020), retrieved on Jun. 24, 2022 from https://en.wikipedia.org/w/index.php?title=Perfusion&oldid=996968059; 5 pages.
Winter et al., "Psilocybin-induced stimulus control in the rat", Pharmacology Biochemistry and Behavior (2007); 87(4): 472-480. doi: 10.1016/j.pbb.2007.06.003. Epub Jun. 22, 2007.
Winter et al., "The Paradox of 5-Methoxy-N, N-Dimethyltryptamine: An Indoleamine Hallucinogen That Induces Stimulus Control Via 5-HT1A Receptors," Pharmacology Biochemistry and Behavior, 2000, vol. 65, No. 1, pp. 75-82.
Wolff, M., "Burger's Medicinal Chemistry And Drug Discovery", Fifth Edition, John Wiley & Sons (1995); 1: 975-977.
Wood et al., "Prevalence of use and acute toxicity associated with the use of NBOMe drugs", Clin Toxicol (Phila). Feb. 2015; 53(2): 85-92. doi:10.3109/15563650.2015.1004179.
Yu, A.M., "Indolealkylamines: Biotransformations and Potential Drug-Drug Interactions," The AAPS Journal, Jun. 2008, vol. 10, No. 2, pp. 242-253.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018. 22 pages.

* cited by examiner

COMPOSITIONS OF MATTER AND PHARMACEUTICAL COMPOSITIONS

CROSS-REFERENCES TO RELATED APPLICATIONS

This application is a continuation of U.S. patent application Ser. No. 18/229,286, filed on Aug. 2, 2023, now U.S. Pat. No. 12,053,453, which is a continuation of U.S. patent application Ser. No. 17/314,107, filed May 7, 2021, now U.S. Pat. No. 11,759,452 on Sep. 19, 2023, and which claims the benefit of U.S. Provisional Application 63/021,866 filed May 8, 2020, U.S. Provisional Application 63/106,516 filed Oct. 28, 2020 and U.S. Provisional Application 63/134,805 filed Jan. 7, 2021.

FIELD OF THE DISCLOSURE

The present invention relates to novel indole compounds, the administration of psilocybin, psilocybin chemical analogues, and novel indole chemical compounds; and pharmaceutical compositions, methods of preparing the pharmaceutical compositions and methods of treating neurological diseases or disorders using the analogues and novel compounds.

BACKGROUND OF THE INVENTION

Psychoactive drugs are compounds that affect behavior, mood, thoughts, or perception. Psychoactive drugs include antipsychotics, anti-anxiety agents, stimulants, reuptake inhibitors, monoamine oxidase inhibitors (MAOI), tricyclic antidepressants and mood stabilizers. Some of these compounds have historically been used for off label psychoactive activity and are now being investigated for positive clinical efficacy. In addition to potential therapeutic efficacy, these drugs must be investigated for all relevant pharmaceutical characteristics, including minimum and maximum dosing thresholds and the most efficacious delivery system.

Indole compounds represent a diverse class of compounds with broad biomedical potential across many targets including cancer, cardiovascular, gastrointestinal, and a wide range of neurological disorders. During in vivo biosynthesis, the amino acid tryptophan precursor of serotonin has been the scaffold of choice for many drugs containing the heterocyclic indole backbone. Serotonin (5-HT) supports many important bodily functions including mood, sleep, appetite, intestinal motility, and sexual health. The serotonergic system consists of a class of G-coupled protein receptors, $5-HT_1$ through $5-HT_7$ as well as their subtypes (1A, 2A, 2B, etc.), which modulate the range of these biological pathways.

Most serotonergic targeting therapeutics are antidepressants either as selective reuptake inhibitors (collectively SSRIs), direct 5-HT modulators (atypical) or in combination with norepinephrine inhibitors (SNRIs). While still not fully understood, the general mechanism of action of the approved therapeutics relies on increasing the concentration of the monoamines, 5-HT and norepinephrine, in the post-synaptic receptors to restore synaptic balance. However these medications generally lack efficacy (being only 20-30% effective over placebo), have considerable side effects, and have a delayed onset of weeks to months.

Sigma-1 receptor ($\sigma$ receptors) are intracellular receptors expressed in specific regions of the brain. Modulation, and agonism, of Sigma-1 ($\sigma_1$) has been shown to have positive impacts on locomotion, mood disorders, increases of brain-derived neurotrophic factor (BDNF), neuronal growth, and neurogenesis. Diverse classes of psychotropic drugs, including antipsychotics, antidepressants, selective serotonin reuptake inhibitors (SSRI's) and motor neuron drugs bind to the ($\sigma_1$) receptor. Binding of the SSRI's to the al receptor may mediate the serotonin independent actions of this class of drugs. The hallucinogen N,N-dimethyltryptamine (DMT) is an endogenous σ1 receptor regulator.

Psilocybin is an indole alkaloid and a naturally occurring psychoactive prodrug that is produced by more than 200 species of mushrooms. Psilocybin is a prodrug that is dephosphorylated in vivo via oral dosing to produce the active compound psilocin. Psilocybin and psilocin are both indole compounds and are known to be potent 5-HT agonists and can cross the blood-brain barrier. The therapeutic implications of psilocybin are broad with active clinical studies targeting depression, anxiety, migraines, addiction, dementias, Alzheimer's disease, eating disorders, obsessive compulsive disorder, and palliative care.

Magic Mushrooms is a common term for a group of over 200 species of naturally occurring mushrooms that contains psilocybin and active psilocybin chemical analogues and combinations thereof. Similarly, other naturally-occurring psychedelic indole compounds include N,N-dimethyltryptamine (DMT), 5-methoxy-DMT (5-MeO-DMT), lysergamides (e.g. LSD), and ibogaine. The raw fruit as well as extracts containing these natural products have been orally consumed for their psychoactive effects. Exact dose response activity has been difficult to quantify because of the variability of the individual response, the difficulty in measuring the potency of the natural organisms and extracts, and the different inherent potencies and ratio of the different analogues and combinations thereof. This is only exacerbated by the interplay of serotonin receptors activities as well as Sigma-1 ($\sigma_1$) receptors, especially for compounds like DMT. Specifically for neurodegenerative diseases and cognitive function, agonists of the $\sigma_1$ receptor (e.g. DMT) are shown to enhance brain plasticity with key roles in memory and learning.

Psilocybin and it's known analogues have been synthesized and bioengineered. In the mid-twentieth century, Sandoz Pharmaceuticals briefly marketed an oral formulation of psilocybin for adjuvant therapy in psychotherapy. The product was soon removed from the market due to the unpredictability of individual response to the dosage form. As of 2020, the U.S. Drug Enforcement Agency has classified psilocybin as a Schedule 1 drug having a high potential for abuse, no approved medical use and a lack of accepted safety for use under medical supervision.

Dosing and assessing pharmaceutical efficacy for these compounds has proven to be difficult. One reason is that plasma concentration-time curves are highly variable. Additionally, psilocybin and especially DMT is subject to first pass metabolism of the oral dosage forms, which reduces availability of active pharmaceutical ingredient before it has entered the systemic circulation. Also, there are wide individual variances in the renal excretion of the compounds. Further, the pH and monoamine oxidase (MAO) enzymatic cleavage of psilocybin to the active pharmaceutical ingredient psilocin after oral delivery can also be a determining factor for the pharmacodynamics. Consequently, research into optimal dosage to treat various neurological disorders has not been rigorously pursued.

A 2016 Johns Hopkins study reported that relatively large doses such as 0.2 mg/kg dosing regimens are needed to induce psychedelic effects, which correlate to blood plasma concentrations between 4-8 ng/mL. The in vivo half-life for psilocin is about 50 minutes and leads to psychedelic experiences lasting 4-6 hours in which trained professionals monitor subjects in a clinical setting. Psychotherapy is performed before and after psychedelic doses to ready the patient and integrate the experiential outcome into a personal response to ameliorate depressive thoughts and actions, with the drug merely acting as a holistic tool. However, in-patient therapies incur significant costs for the patient and time on the care provider, not to mention the increased risk for adverse events while a patient is under the influence of a psychedelic drug.

Additionally, the positive psychological effects were seen with increasing doses, but the negative side effects of anxiety, negative ideation, nausea, and headaches also increased as doses increased. Consequently, professional monitoring of the patients is necessary before, during and after the psychedelic session. Recently, microdosing has been used to dose psychedelic substances in very small, sub-perceptual amounts. Psychedelic substances that have been microdosed include LSD (lysergic acid diethylamide), cannabis and psilocybin analogues. Reports of microdosing substances such as DMT and 5-MeO-DMT are scant since their lack of bioavailability and short half-life makes their dosing challenging. Microdosing has been reported to have the beneficial therapeutic effects of improving mood, intellectual focus, energy levels, and creativity without the disabling hallucinogenic effects.

Microdosing of a psychedelic substance largely reduces psychotropic effects and anecdotally dosing is usually one-tenth ($1/10^{th}$) of a psychedelic dose. Many clinical investigations of psychedelics to alleviate depression and PTSD omit participants with a history of heart trouble, psychosis, and schizophrenia since the intense psychotropic effects can exacerbate these conditions microdosing could alleviate these issues. Treatments that are devoid of psychedelic effects would make the administration of the drugs in a clinical setting unnecessary, opening more traditional, flexible, and affordable drug regimens. Microdosing reports have noted improved cognitive benefits such as productivity, creativity, and abstract thinking; coupling evidence suggesting psychedelics reduce neuroinflammation and increase neuroplasticity and neuronal connections could lead to effective treatments for dementia, Alzheimer's disease, and other neurocognitive disorders.

Transdermal and nasal application of active pharmaceutical ingredients has many benefits when used for psychoactive drugs. In particular, psilocin is the product of the conversion of psilocybin, which is a prodrug that is transformed to psilocin in the gastrointestinal tract. By avoiding the gastrointestinal tract through transdermal application of psilocin problems with absorption and food interactions can be avoided. As therapeutic effects of orally-dosed DMT can only be realized with co-administration of MAOIs, transdermal systems offer a new delivery method with reduced metabolism and improved pharmacokinetic/pharmacodynamic (PK/PD) properties. Other benefits of transdermal dosing include avoiding of the first pass metabolism; providing multi-day therapy by single application thereby improving patient compliance; and extending the activity of drugs having short half-life through the reservoir of drug present in the delivery system and its controlled release characteristics.

Systemic delivery of pharmaceutical ingredients by administration to the nasal mucosa can be advantageous. Nasal delivery allows for avoidance of intestinal metabolism and first pass metabolism. Additionally, nasal delivery of systemic drugs can bypass the blood brain barrier and enter the brain via the olfactory and trigeminal nerve pathways, which can be advantageous for pharmaceutical dosing of diseases of the central nervous system. An additional benefit of nasal dosing is the rapid systemic absorption through the nasal mucosa; pairing this with a short half-life compound like DMT could have significant clinical advantages over longer acting psychedelics.

Oral delivery of drugs is often preferred over various other drug administration routes because of ease of ingestion, pain avoidance, good patient compliance and compounding history. However, many problems are still associated with oral delivery such as poor solubility of drugs in aqueous environments, taste, stability of the drug with the formulation excipients, varied dissolution rates, unknown gastrointestinal absorption issues and food effects. Oral pharmaceutical formulations are recognized as a scientific endeavor that requires specific knowledge of the field in general, and innovative design.

Recent studies on psilocybin and its psilocybin analogues and combinations thereof, have been reported to have efficacy in models and small clinical trials of post-treatment Lyme disease syndrome, dementias, Alzheimer's disease, post-traumatic stress disorder, anorexia nervosa, depression and anxiety, abuse disorders including opioid addiction, alcohol addiction, nicotine addiction, cannabinoid addiction, headache, central nervous system inflammation, dementia, and disorders of cognition and memory. These promising experimental reports using psilocybin and its analogues demonstrate an immediate need to determine a formulation to permit the most advantageous dosing amount and dosing period; improved pharmacokinetic (PK) profiles, pharmacodynamic (PD) profiles, or safety profiles; evaluation of the benefits of long term or maintenance therapies; development of treatment regimens that maximize biological efficacy for treating diseases; and the use of these compounds in other potential advantageous benefits. Additionally, there is a need for development of novel, safe and effective exogenous serotonergic and/or Sigma-1 modulators for the treatment of neurological, mood and abuse disorders or diseases.

SUMMARY

Provided herein are novel indole compounds that have biological efficacy and increased clinical safety.

These compounds include the compounds of Structure (1) or pharmaceutically acceptable salts or solvates thereof:

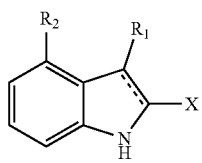

Structure (1)

wherein:
X is H, $CF_3$, or a halogen that is selected from the group consisting of F, Cl, Br, I, and astatine; $R_1$ comprises an aliphatic substituent with a primary, secondary, tertiary, or quaternary amine; $R_2$ is hydrogen, hydroxyl, ester, ether, aldehyde, acid, amide, thiol, sulfones, sulfonamide or combinations thereof.

A further aspect of the present invention is a compound according to Structure (1), as described above, that is selected from the group consisting of:

TABLE 1

NOVEL INDOLE COMPOUNDS 2-bromo-3-[2-(dimethylamino)ethyl]-1H-indol-4-ol
2-fluoro-3-[2-(dimethylamino)ethyl]-1H-indol-4-ol
2-chloro-3-[2-(dimethylamino)ethyl]-1H-indol-4-ol
2-iodo-3-[2-(dimethylamino)ethyl]-1H-indol-4-ol
3-[2-(dimethylamino)ethyl]-2-trifluoromethyl-1H-indol-4-ol
2-bromo-3-[2-(dimethylamino)ethyl]-1H-indol-4-yl dihydrogen phosphate
2-fluoro-3-[2-(dimethylamino)ethyl]-1H-indol-4-yl dihydrogen phosphate
2-chloro-3-[2-(dimethylamino)ethyl]-1H-indol-4-yl dihydrogen phosphate
2-iodo-3-[2-(dimethylamino)ethyl]-1H-indol-4-yl dihydrogen phosphate
3-[2-(dimethylamino)ethyl]-2-trifluoromethyl-1H-indol-4-yl dihydrogen phosphate
2-bromo-3-[2-(dimethylammonio)ethyl]-1H-indol-4-yl hydrogen phosphate
2-fluoro-3-[2-(dimethylammonio)ethyl]-1H-indol-4-yl hydrogen phosphate
2-chloro-3-[2-(dimethylammonio)ethyl]-1H-indol-4-yl hydrogen phosphate
2-iodo-3-[2-(dimethylammonio)ethyl]-1H-indol-4-yl hydrogen phosphate
3-[2-(dimethylammonio)ethyl]-2-trifluoromethyl-1H-indol-4-yl hydrogen phosphate
2-(2-bromo-1H-indol-3-yl)-N,N-dimethylethan-1-amine
2-(2-fluoro-1H-indol-3-yl)-N,N-dimethylethan-1-amine
2-(2-chloro-1H-indol-3-yl)-N,N-dimethylethan-1-amine
2-(2-iodo-1H-indol-3-yl)-N,N-dimethylethan-1-amine
N N-dimethyl-2-(2-trifluoromethyl-1H-indol-3-yl)ethan-1amine
3-[2-(dimethylamino)ethyl]-1H-indol-4-yl acetate
2-bromo-3-[2-(dimethylamino)ethyl]-1H-indol-4-yl acetate
2-fluoro-3-[2-(dimethylamino)ethyl]-1H-indol-4-yl acetate
2-chloro-3-[2-(dimethylamino)ethyl]-1H-indol-4-yl acetate
2-iodo-3-[2-(dimethylamino)ethyl]-1H-indol-4-yl acetate
3-[2-(dimethylamino)ethyl]-2-trifluoromethyl-1H-indol-4-yl acetate
3-[2-(dimethylamino)ethyl]-1H-indol-4-yl propionate
2-bromo-3-[2-(dimethylamino)ethyl]-1H-indol-4-yl propionate
2-fluoro-3-[2-(dimethylamino)ethyl]-1H-indol-4-yl propionate
2-chloro-3-[2-(dimethylamino)ethyl]-1H-indol-4-yl propionate
2-iodo-3-[2-(dimethylamino)ethyl]-1H-indol-4-yl propionate
3-[2-(dimethylamino)ethyl]-2-trifluoromethyl-1H-indol-4-yl propionate
3-[2-(dimethylamino)ethyl]-1H-indol-4-yl butyrate
2-bromo-3-[2-(dimethylamino)ethyl]-1H-indol-4-yl butyrate
2-fluoro-3-[2-(dimethylamino)ethyl]-1H-indol-4-yl butyrate
2-chloro-3-[2-(dimethylamino)ethyl]-1H-indol-4-yl butyrate
2-iodo-3-[2-(dimethylamino)ethyl]-1H-indol-4-yl butyrate
3-[2-(dimethylamino)ethyl]-2-trifluoromethyl-1H-indol-4-yl butyrate
3-[2-(dimethylamino)ethyl]-1H-indol-4-yl pentanoate
2-bromo-3-[2-(dimethylamino)ethyl]-1H-indol-4-yl pentanoate
2-fluoro-3-[2-(dimethylamino)ethyl]-1H-indol-4-yl pentanoate
2-chloro-3-[2-(dimethylamino)ethyl]-1H-indol-4-yl pentanoate
2-iodo-3-[2-(dimethylamino)ethyl]-1H-indol-4-yl pentanoate
3-[2-(dimethylamino)ethyl]-2-trifluoromethyl-1H-indol-4-yl pentanoate
3-[2-(dimethylamino)ethyl]-1H-indol-4-yl hexanoate
2-bromo-3-[2-(dimethylamino)ethyl]-1H-indol-4-yl hexanoate
2-fluoro-3-[2-(dimethylamino)ethyl]-1H-indol-4-yl hexanoate
2-chloro-3-[2-(dimethylamino)ethyl]-1H-indol-4-yl hexanoate
2-iodo-3-[2-(dimethylamino)ethyl]-1H-indol-4-yl hexanoate
3-[2-(dimethylamino)ethyl]-2-trifluoromethyl-1H-indol-4-yl hexanoate
3-[2-(dimethylamino)ethyl]-1H-indol-4-yl heptanoate
2-bromo-3-[2-(dimethylamino)ethyl]-1H-indol-4-yl heptanoate
2-fluoro-3-[2-(dimethylamino)ethyl]-1H-indol-4-yl heptanoate
2-chloro-3-[2-(dimethylamino)ethyl]-1H-indol-4-yl heptanoate
2-iodo-3-[2-(dimethylamino)ethyl]-1H-indol-4-yl heptanoate
3-[2-(dimethylamino)ethyl]-2-trifluoromethyl-1H-indol-4-yl heptanoate
3-[2-(dimethylamino)ethyl]-1H-indol-4-yl octanoate
2-bromo-3-[2-(dimethylamino)ethyl]-1H-indol-4-yl octanoate
2-fluoro-3-[2-(dimethylamino)ethyl]-1H-indol-4-yl octanoate
2-chloro-3-[2-(dimethylamino)ethyl]-1H-indol-4-yl octanoate
2-iodo-3-[2-(dimethylamino)ethyl]-1H-indol-4-yl octanoate
3-[2-(dimethylamino)ethyl]-2-trifluoromethyl-1H-indol-4-yl octanoate,
3-[2-(dimethylamino)ethyl]-1H-indol-4-yl nonanoate
2-bromo-3-[2-(dimethylamino)ethyl]-1H-indol-4-yl nonanoate
2-fluoro-3-[2-(dimethylamino)ethyl]-1H-indol-4-yl nonanoate
2-chloro-3-[2-(dimethylamino)ethyl]-1H-indol-4-yl nonanoate
2-iodo-3-[2-(dimethylamino)ethyl]-1H-indol-4-yl nonanoate
3-[2-(dimethylamino)ethyl]-2-trifluoromethyl-1H-indol-4-yl nonanoate
3-[2-(dimethylamino)ethyl]-1H-indol-4-yl decanoate
2-bromo-3-[2-(dimethylamino)ethyl]-1H-indol-4-yl decanoate,
2-fluoro-3-[2-(dimethylamino)ethyl]-1H-indol-4-yl decanoate,
2-chloro-3-[2-(dimethylamino)ethyl]-1H-indol-4-yl decanoate,
2-iodo-3-[2-(dimethylamino)ethyl]-1H-indol-4-yl decanoate
3-[2-(dimethylamino)ethyl]-2-trifluoromethyl-1H-indol-4-yl decanoate
3-[2-(dimethylamino)ethyl]-1H-indol-4-yl undecanoate
2-bromo-3-[2-(dimethylamino)ethyl]-1H-indol-4-yl undecanoate
2-fluoro-3-[2-(dimethylamino)ethyl]-1H-indol-4-yl undecanoate
2-chloro-3-[2-(dimethylamino)ethyl]-1H-indol-4-yl undecanoate TABLE 1-continued

NOVEL INDOLE COMPOUNDS 2-iodo-3-[2-(dimethylamino)ethyl]-1H-indol-4-yl undecanoate
3-[2-(dimethylamino)ethyl]-2-trifluoromethyl-1H-indol-4-yl undecanoate
3-[2-(dimethylamino)ethyl]-1H-indol-4-yl dodecanoate
2-bromo-3-[2-(dimethylamino)ethyl]-1H-indol-4-yl dodecanoate
2-fluoro-3-[2-(dimethylamino)ethyl]-1H-indol-4-yl dodecanoate
2-chloro-3-[2-(dimethylamino)ethyl]-1H-indol-4-yl dodecanoate
2-iodo-3-[2-(dimethylamino)ethyl]-1H-indol-4-yl dodecanoate
3-[2-(dimethylamino)ethyl]-2-trifluoromethyl-1H-indol-4-yl dodecanoate
2-(4-methoxy-1H-indol-3-yl)-N,N-dimethylethan-1-amine
2-(2-bromo-4-methoxy-1H-indol-3-yl)-N N-dimethylethan-1-amine
2-(2-fluoro-4-methoxy-1H-indol-3-yl)-N,N-dimethylethan-1-amine
2-(2-chloro-4-methoxy-1H-indol-3-yl)-N,N-dimethylethan-1-amine
2-(2-iodo-4-methoxy-1H-indol-3-yl)-N,N-dimethylethan-1-amine
2-(4-methoxy-2-trifluoromethyl-1H-indol-3-yl)-N,N-dimethylethan-1-amine
1-[3-[2-(dimethylamino)ethyl]-1H-indol-4-yl]ethan-1-one
1-[2-bromo-3-[2-(dimethylamino)ethyl]-1H-indol-4-yl]ethan-1-one
1-[2-fluoro-3-[2-(dimethylamino)ethyl]-1H-indol-4-yl]ethan-1-one,
1-[2-chloro-3-[2-(dimethylamino)ethyl]-1H-indol-4-yl]ethan-1-one
1-[2-iodo-3-[2-(dimethylamino)ethyl]-1H-indol-4-yl]ethan-1-one
1-[3-[2-(dimethylamino)ethyl]-2-trifluoromethyl-1H-indol-4-yl]ethan-1-one
3-[2-(dimethylamino)ethyl]-1H-indole-4-carboxylic acid
2-bromo-3-[2-(dimethylamino)ethyl]-1H-indole-4-carboxylic acid
2-fluoro-3-[2-(dimethylamino)ethyl]-1H-indole-4-carboxylic acid
2-chloro-3-[2-(dimethylamino)ethyl]-1H-indole-4-carboxylic acid
2-iodo-3-[2-(dimethylamino)ethyl]-1H-indole-4-carboxylic acid
3-[2-(dimethylamino)ethyl]-2-trifluoromethyl-1H-indole-4-carboxylic acid
3-[2-(dimethylamino)ethyl]1H-indole-4 methyl carboxylate
2-bromo-3-[2-(dimethylamino)ethyl]1H-indole-4 methyl carboxylate
2-fluoro-3-[2-(dimethylamino)ethyl]1H-indole-4 methyl carboxylate
2-chloro-3-[2-(dimethylamino)ethyl]1H-indole-4 methyl carboxylate
2-iodo-3-[2-(dimethylamino)ethyl]1H-indole-4 methyl carboxylate
3-[2-(dimethylamino)ethyl]-2-trifluoromethyl-1H-indole-4 methyl carboxylate
3-[2-(dimethylamino)ethyl]1H-indole-4 ethyl carboxylate
2-bromo-3-[2-(dimethylamino)ethyl]1H-indole-4 ethyl carboxylate
2-fluoro-3-[2-(dimethylamino)ethyl]1H-indole-4 ethyl carboxylate
2-chloro-3-[2-(dimethylamino)ethyl]1H-indole-4 ethyl carboxylate
2-iodo-3-[2-(dimethylamino)ethyl]1H-indole-4 ethyl carboxylate
3-[2-(dimethylamino)ethyl]-2-trifluoromethyl-1H-indole-4 ethyl carboxylate
3-[2-(dimethylamino)ethyl]1H-indole-4 propyl carboxylate
2-bromo-3-[2-(dimethylamino)ethyl]1H-indole-4 propyl carboxylate
2-fluoro-3-[2-(dimethylamino)ethyl]1H-indole-4 propyl carboxylate
2-chloro-3-[2-(dimethylamino)ethyl]1H-indole-4 propyl carboxylate
2-iodo-3-[2-(dimethylamino)ethyl]1H-indole-4 propyl carboxylate
3-[2-(dimethylamino)ethyl]-2-trifluoromethyl-1H-indole-4 propyl carboxylate
3-[2-(dimethylamino)ethyl]1H-indole-4 butyl carboxylate
2-bromo-3-[2-(dimethylamino)ethyl]1H-indole-4 butyl carboxylate
2-fluoro-3-[2-(dimethylamino)ethyl]1H-indole-4 butyl carboxylate
2-chloro-3-[2-(dimethylamino)ethyl]1H-indole-4 butyl carboxylate
2-iodo-3-[2-(dimethylamino)ethyl]1H-indole-4 butyl carboxylate
3-[2-(dimethylamino)ethyl]-2-trifluoromethyl-1H-indole-4 butyl carboxylate
3-[2-(dimethylamino)ethyl]1H-indole-4 pentyl carboxylate
2-bromo-3-[2-(dimethylamino)ethyl]1H-indole-4 pentyl carboxylate
2-fluoro-3-[2-(dimethylamino)ethyl]1H-indole-4 pentyl carboxylate
2-chloro-3-[2-(dimethylamino)ethyl]1H-indole-4 pentyl carboxylate
2-iodo-3-[2-(dimethylamino)ethyl]1H-indole-4 pentyl carboxylate
3-[2-(dimethylamino)ethyl]-2-trifluoromethyl-1H-indole-4 pentyl carboxylate
3-[2-(dimethylamino)ethyl]1H-indole-4 hexyl carboxylate
2-bromo-3-[2-(dimethylamino)ethyl]1H-indole-4 hexyl carboxylate
2-fluoro-3-[2-(dimethylamino)ethyl]1H-indole-4 hexyl carboxylate
2-chloro-3-[2-(dimethylamino)ethyl]1H-indole-4 hexyl carboxylate
2-iodo-3-[2-(dimethylamino)ethyl]1H-indole-4 hexyl carboxylate
3-[2-(dimethylamino)ethyl]-2-trifluoromethyl-1H-indole-4 hexyl carboxylate
3-[2-(dimethylamino)ethyl]1H-indole-4 heptyl carboxylate
2-bromo-3-[2-(dimethylamino)ethyl]1H-indole-4 heptyl carboxylate
2-fluoro-3-[2-(dimethylamino)ethyl]1H-indole-4 heptyl carboxylate
2-chloro-3-[2-(dimethylamino)ethyl]1H-indole-4 heptyl carboxylate
2-iodo-3-[2-(dimethylamino)ethyl]1H-indole-4 heptyl carboxylate
3-[2-(dimethylamino)ethyl]-2-trifluoromethyl-1H-indole-4 heptyl carboxylate
3-[2-(dimethylamino)ethyl]1H-indole-4 octyl carboxylate
2-bromo-3-[2-(dimethylamino)ethyl]1H-indole-4 octyl carboxylate
2-fluoro-3-[2-(dimethylamino)ethyl]1H-indole-4 octyl carboxylate
2-chloro-3-[2-(dimethylamino)ethyl]1H-indole-4 octyl carboxylate
2-iodo-3-[2-(dimethylamino)ethyl]1H-indole-4 octyl carboxylate
3-[2-(dimethylamino)ethyl]-2-trifluoromethyl-1H-indole-4 octyl carboxylate
3-[2-(dimethylamino)ethyl]1H-indole-4 nonyl carboxylate
2-bromo-3-[2-(dimethylamino)ethyl]1H-indole-4 nonyl carboxylate
2-fluoro-3-[2-(dimethylamino)ethyl]1H-indole-4 nonyl carboxylate
2-chloro-3-[2-(dimethylamino)ethyl]1H-indole-4 nonyl carboxylate TABLE 1-continued

NOVEL INDOLE COMPOUNDS 2-iodo-3-[2-(dimethylamino)ethyl]1H-indole-4 nonyl carboxylate
3-[2-(dimethylamino)ethyl]-2-trifluoromethyl-1H-indole-4 nonyl carboxylate
3-[2-(dimethylamino)ethyl]1H-indole-4 decyl carboxylate
2-bromo-3-[2-(dimethylamino)ethyl]1H-indole-4 decyl carboxylate
2-fluoro-3-[2-(dimethylamino)ethyl]1H-indole-4 decyl carboxylate
2-chloro-3-[2-(dimethylamino)ethyl]1H-indole-4 decyl carboxylate
2-iodo-3-[2-(dimethylamino)ethyl]1H-indole-4 decyl carboxylate
3-[2-(dimethylamino)ethyl]-2-trifluoromethyl-1H-indole-4 decyl carboxylate
3-[2-(dimethylamino)ethyl]1H-indole-4 undecyl carboxylate
2-bromo-3-[2-(dimethylamino)ethyl]1H-indole-4 undecyl carboxylate
2-fluoro-3-[2-(dimethylamino)ethyl]1H-indole-4 undecyl carboxylate
2-chloro-3-[2-(dimethylamino)ethyl]1H-indole-4 undecyl carboxylate
2-iodo-3-[2-(dimethylamino)ethyl]1H-indole-4 undecyl carboxylate
3-[2-(dimethylamino)ethyl]-2-trifluoromethyl-1H-indole-4 undecyl carboxylate
3-[2-(dimethylamino)ethyl]1H-indole-4 dodecyl carboxylate
2-bromo-3-[2-(dimethylamino)ethyl]1H-indole-4 dodecyl carboxylate
2-fluoro-3-[2-(dimethylamino)ethyl]1H-indole-4 dodecyl carboxylate
2-chloro-3-[2-(dimethylamino)ethyl]1H-indole-4 dodecyl carboxylate
2-iodo-3-[2-(dimethylamino)ethyl]1H-indole-4 dodecyl carboxylate
3-[2-(dimethylamino)ethyl]-2-trifluoromethyl-1H-indole-4 dodecyl carboxylate
1-[3-[2-(dimethylamino)ethyl]-1H-indol-4-yl]-N-methylmethanesulfonamide
1-[2-bromo-3-[2-(dimethylamino)ethyl]-1H-indol-4-yl]-N-methylmethanesulfonamide
1-[2-fluoro-3-[2-(dimethylamino)ethyl]-1H-indol-4-yl]-N-methylmethanesulfonamide
1-[2-chloro-3-[2-(dimethylamino)ethyl]-1H-indol-4-yl]-N-methylmethanesulfonamide
1-[2-iodo-3-[2-(dimethylamino)ethyl]-1H-indol-4-yl]-N-methylmethanesulfonamide
1-[3-[2-(dimethylamino)ethyl]-2-trifluoromethyl-1H-indol-4-yl]-N-methylmethanesulfonamide
and any salt forms thereof.

In another aspect of this invention, are the compounds of Structure (2) or pharmaceutically acceptable salts or solvates thereof:

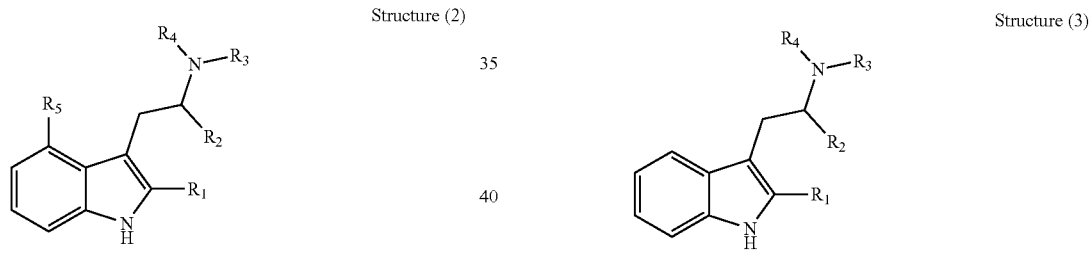

Structure (2)

wherein $R_1$ is selected from the group consisting of H, F, Cl, Br, I, or $CF_3$; $R_2$ or $CH_3$; $R_3$ and $R_4$ are each independently optionally selected from the group consisting of H, $CH_3$, $C_2H_5$, $(H_3C)_2CH$, or $H_2C=CH-CH_2$; wherein $R_5$ is selected from the group consisting of $OCH_3$, $OCOCH_3$, O-phosphate, O-polyethylene glycol (PEG), $O-(CH_2)_2(COOH)_2$ (succinate), $O-(CH_2)_2(COOH)$ (hemi-succinate), and $CH_2SO_2NHCH_3$ (sulfonamide); wherein when $R_1$ is H then $R_5$ is $CH_2SO_2NHCH_3$.

Specific compounds of Structure (2) are 2-chloro-3-(2-(dimethylamino)ethyl)-1H-indol-4-yl acetate, 2-bromo-3-(2-(dimethylamino)ethyl)-1H-indol-4-yl acetate, 2-chloro-3-(2-(dimethylamino)ethyl)-1H-indol-4-yl hydrogen phosphate, 2-bromo-3-(2-(dimethylamino)ethyl)-1H-indol-4-yl hydrogen phosphate, 2-bromo-3-(2-(dimethylamino)ethyl)-1H-indol-4-ol, 2-chloro-3-(2-(dimethylamino)ethyl)-1H-indol-4-ol, 2-(2-chloro-4-methoxy-1H-indol-3-yl)-N,N-dimethylethan-1-amine, 2-(2-bromo-4-methoxy-1H-indol-3-yl)-N,N-dimethylethan-1-amine. Other specific compounds of Structure (2) are of particular interest are 1-(2-chloro-3-(2-(dimethylamino)ethyl)-1H-indol-4-yl)-N-methylmethanesulfonamide, 1-(2-bromo-3-(2-(dimethylamino)ethyl)-1H-indol-4-yl)-N-methylmethanesulfonamide, and 1-(3-(2-(dimethylamino)ethyl)-1H-indol-4-yl)-N-methylmethanesulfonamide Another aspect of this invention, are the compounds of Structure (3) or pharmaceutically acceptable salts or solvates thereof:

Structure (3)

wherein $R_1$ is selected from the group consisting of F, Cl, Br, I, or $CF_3$; $R_2$ is $CH_3$; $R_3$ and $R_4$ are each independently optionally selected from the group consisting of H, $CH_3$, $C_2H_5$, $(H_3C)_2CH$, or $H_2C=CH-CH_2$ Specific compounds of Structure (3) are 2-(2-chloro-1H-indol-3-yl)-N,N-dimethylethan-1-amine, 2-(2-chloro-1H-indol-3-yl)-N,N-dimethylethan-1-amine, (R)-1-(2-chloro-1H-indol-3-yl)propan-2-amine, (R)-1-(2-chloro-1H-indol-3-yl)-N-methylpropan-2-amine, (R)-1-(2-chloro-1H-indol-3-yl)-N,N-dimethylpropan-2-amine, (S)-1-(2-chloro-1H-indol-3-yl)-N,N-dimethylpropan-2-amine, (S)-1-(2-chloro-1H-indol-3-yl)propan-2-amine, (S)-1-(2-chloro-1H-indol-3-yl)-N-methylpropan-2-amine, (R)-1-(2-bromo-1H-indol-3-yl)propan-2-amine, (R)-1-(2-bromo-1H-indol-3-yl)-N-methylpropan-2-amine, (R)-1-(2-bromo-1H-indol-3-yl)-N,N-dimethylpropan-2-amine, (S)-1-(2-bromo-1H-indol-3-yl)-N,N-dimethylpropan-2-amine, (S)-1-(2-bromo-1H-indol-3-yl)propan-2-amine, (S)-1-(2-bromo-1H-indol-3-yl)-N-methylpropan-2-amine, 2-(2-chloro-1H-indol-3-yl)-N,N-diethylethane-1-amine, N-(2-(2-chloro-1H-indol-3-yl)ethyl)-N-isopropylpropan-2-amine, N-(2-(2-chloro-1H-indol-3-yl)ethyl)-N-vinylethenamine, 2-(2-bromo-1H-indol-3-yl)-N,N-diethylethan-1-amine, N-(2-(2-bromo-1H- indol-3-yl)ethyl)-N-isopropylpropan-2-amine, or N-(2-(2-bromo-1H-indol-3-yl)ethyl)-N-isopropylpropan-2-amine.

Provided herein are pharmaceutical compositions wherein the compositions are designed to release the active pharmaceutical ingredients as described herein into the bloodstream through the application of the active pharmaceutical ingredient transdermally to the skin and nasal passages. These pharmaceutical compositions are transdermal or nasal pharmaceutical formulations. The active pharmaceutical ingredient may be applied by sprayable liquids, gels, creams, lotions, ointments, transdermal patch and the like.

In one embodiment, the transdermal pharmaceutical and nasal compositions of active pharmaceutical ingredients may be the compounds as described by Structures (1), (2), (3), and the compounds listed in Table (1) and any ionic or salt forms thereof.

In certain embodiments, the psilocybin analogues and combinations hereof, include any compound that is structurally related to psilocybin and functionally mimics and/or antagonizes the action of serotonin. In another embodiment the active pharmaceutical ingredient comprises psilocybin and active analogues and combinations thereof. Active analogues and combinations thereof of psilocybin include but are not limited have the compounds listed in Table (2) Psilocybin Analogues.

TABLE 2

Psilocybin and Psilocybin Analogs psilocybin
psilocin
4-hydroxy-indole-3-acetic acid
4-hydroxy-indole-3-acetaldehyde
4-hydroxytryptophol
4-hydroxytryptophan
norpsilocin
aeruginascin
baeocystin
norbaeocystin
4-hydroxy-N-methyl-N-ethyltryptamine (4-OH-MET)
4-hydroxydiethyltryptamine (4-OH-DET)
4-hydroxy-N,N-dipropyltryptamine (4-OH-DPT
4-hydroxy-N,N-diisopropyltryptamine (4-OH-DiPT
N,N-dimethyltryptamine (DMT)
Indole-3-acetic acid
N,N-dimethyltryptamine-N-oxide (DMT-NO)
lysergic acid diethylamide (LSD)
O-acetylpsilocin (4-AcO-DMT)
5-methoxy-N,N-dimethyltryptamine (5-MeO-DMT
ibogaine
bufotenin (5-OH-DMT)

Provided herein is the manufacture of a transdermal or nasal medicament using as the active pharmaceutical ingredient the novel compounds and described by Structure (1), (2), and (3), the novel compounds listed of Table (1), and the psilocybin analogs of Table (2) and salts or solvates thereof for the treatment of neurological, mood, and abuse disorders or disease.

The transdermal and nasal pharmaceutical compositions of the present invention provide a composition as described for use in a medicine to treat, manage or prevent a disease.

In another embodiment, the pharmaceutical compositions are designed for oral delivery into the human systemic circulation with quick onset and duration.

In another embodiment, the pharmaceutical compositions are designed for extended release into the human systemic circulation via oral delivery, preferably providing a once daily dose.

The oral pharmaceutical compositions described herein may be designed for modified time release of the active pharmaceutical ingredients into the human systemic circulation for extended duration. The composition may be comprised of solid, semisolid, liquid, or flexible delivery systems and administered via sublingual, buccal, or oral administration. The active pharmaceutical ingredient may be supplied within a tablet, capsule, softgels, strip, sublingual strip, wafer, solution, suspensions.

In one embodiment, the oral pharmaceutical compositions contain the active pharmaceutical ingredient of the novel compounds and described by Structures (1), (2), (3), the novel compounds of Table (1), and the psilocybin analogs of Table (2) or salts or solvates thereof. Combinations of psilocybin analogs and/or the novel indole compounds as the active pharmaceutical ingredient of pharmaceutical formulations is also part of the present invention.

The present invention provides a composition as described for use in the treatment, management, or prevention of a neurological, mood, or abuse disorders or disease wherein the disorder may be depression, central nervous system inflammation, addiction, headache, or dementia, or disorders of cognition and memory.

The present invention provides for the combination of the topical, nasal, or oral application of the compounds and analogues described herein in combination with active pharmaceutical ingredients that have been approved by regulatory authority for the treatment, management or preventions of neurological, mood and abuse disorders or disease. The approved active pharmaceutical ingredients may be delivered to a patient in need by any delivery system approved by the regulatory authorities. In one aspect of the present invention, the approved active pharmaceutical ingredient for use in combination with the novel indoles or the psilocybin analogues is a MAOI. In another aspect of the present invention the approved active pharmaceutical ingredient is a 5-HT antagonist.

Also provided herein are novel synthesis pathways to provide the novel indole compounds of Structure (1), (2), and (3), and to the novel compounds of Table (1) and the psilocybin analogs of Table (2). The novel synthesis of the described compounds is described in the specific examples and as described herein.

DETAILED DESCRIPTION

Figure 1:
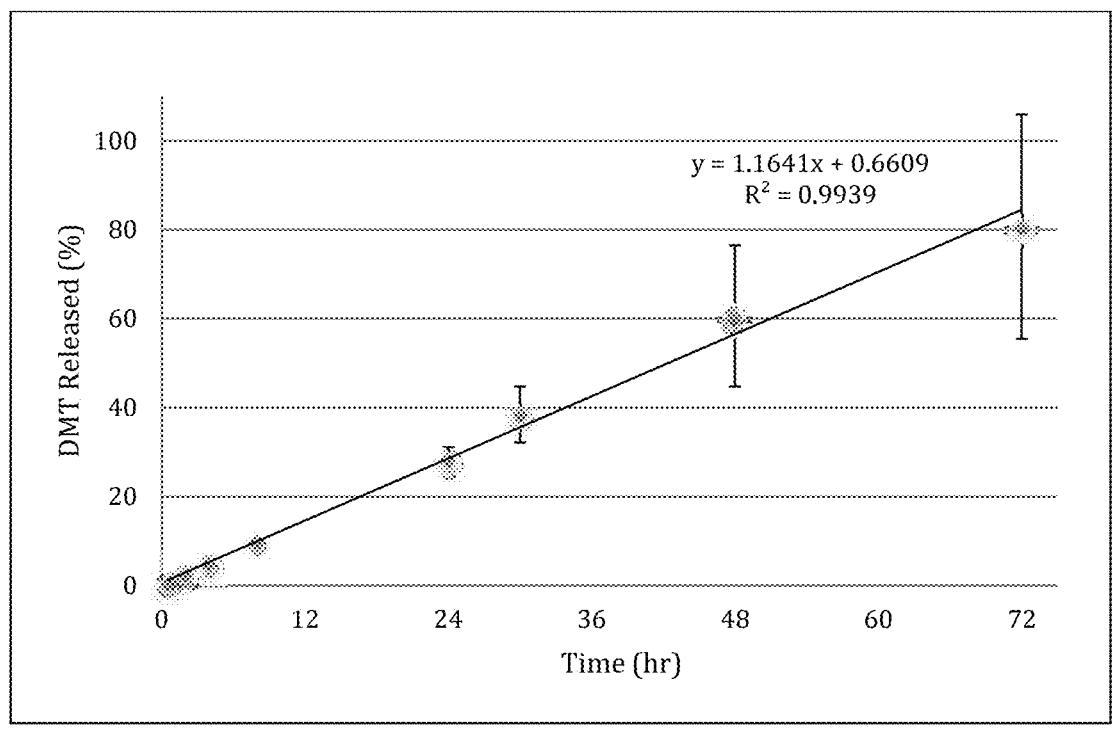
FIG. 1 demonstrates the drug release of DMT transdermal patches from Example 1. The results are averaged (n=3) as assessed by Franz cell diffusion model.
Figure 2:
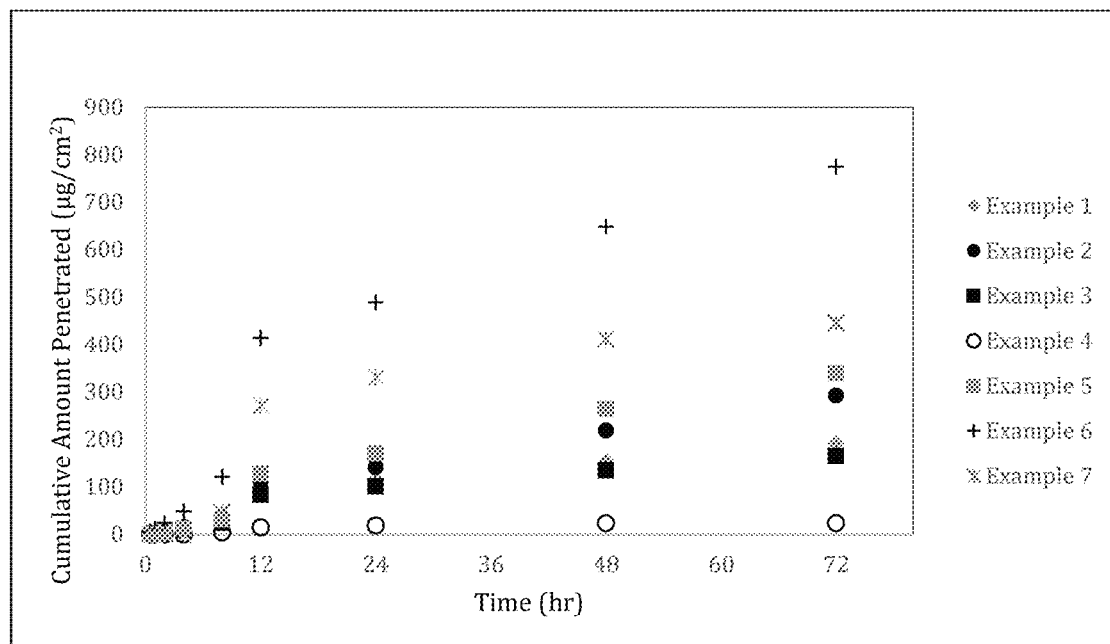
FIG. 2 demonstrates the diffusion rate of the transdermal formulation by the Franz cell model.

Unless defined otherwise, all technical and scientific terms used herein have the same meaning as commonly understood by one of ordinary skill in the art.

As used in the specification and the accompanying claims the indefinite articles "a" and "an" and the definite article "the" include plural as well as singular referents, unless the context clearly dictates otherwise.

The term "about" or approximately" means an acceptable error for a particular value as determined by one of ordinary skill in the art, which depends in part on how the value is measured or determined. In certain embodiments, the term "about" or approximately" means within 1, 2, 3 or 4 standard deviations. In certain embodiments, the term "about" or "approximately" means with 30%, 20%, 15%, 10%, 9%, 8%, 7%, 6%, 5%, 4%, 3%, 2%, 1%, 0.5%, 0.1%, or 0.05%, of a given value or range.

As used herein, and unless otherwise specified, the terms "treat," "treating" and "treatment" refer to the eradication or amelioration of a disease or disorder, or of one or more symptoms associated with the disease or disorder. In certain embodiment the terms refer to minimizing the spread or worsening of the disease or disorder resulting from the administration of one or more prophylactic or therapeutic agents to a subject with such disease or disorder. In some embodiments the terms refer to the administration of a compound or dosage form provided herein, with or without one or more additional active agent(s), after the onset of symptoms of a particular disease.

As used herein, and unless otherwise specified, the term "Abuse Disorder" is a disorder or disease that affects a person's brain and behavior and leads to an inability to control the use of a legal or illegal drug or medication. Prescription medicines, non-prescription medicines, and non-approved drugs may all be abused drugs. Drugs and medication may also include substances such as amphetamines, opioids, cocaine, barbiturates, alcohol, marijuana, and nicotine.

As used herein, and unless otherwise specified, the term "Mood Disorder" is a group of conditions where a disturbance in the person's mood is the underlying feature. Mood disorders may be groups of mania (elevated mood disorders) or hypomania (depression). The classification is in the Diagnostic and Statistical Manual of Mental Disorders (DSM) and the International Classification of Diseases (ICD).

As used herein, and unless otherwise specified, the term "Neurological Disorder" refers to diseases of the central and peripheral nervous system e.g., the brain, spinal cord, cranial nerves, peripheral nerves, nerve roots, autonomic nervous system, neuromuscular junction, and muscles. These disorders include epilepsy, Alzheimer's disease and other dementias, cerebrovascular diseases including stroke, migraine, cluster headaches and other headache disorders, multiple sclerosis, Parkinson's disease, neuroinfections, brain tumors, traumatic disorders of the nervous system due to head trauma, and traumatic disorders due to traumatic or terrifying experiences (Posttraumatic Stress Disorder e.g. PTSD) and neurological disorders as a result of malnutrition and substance abuse. The substance abused may be any number of addictive substances, especially alcohol and drugs and combinations thereof. Many bacterial (e.g., Mycobacterial tuberculosis, *Neisseria meningitides*), viral (e.g. Human Immunodeficiency Virus (HIV), Lyme Disease, Enteroviruses, West Nile Virus, Zika), fungal (e.g., *Cryptococcus, Aspergillus*), and parasitic (e.g., malaria, Chagas) infections can affect the nervous system. Neurological symptoms may occur due to the infection itself, or due to an immune response.

As used herein, and unless otherwise specified, the terms "prevent," "preventing" and "prevention" refer to the prevention of the onset, recurrence or spread of a disease or disorder or of one or more symptoms thereof. In certain embodiments, the terms refer to the treatment with or administration of a compounder dosage form provided herein, with or without one or more other additional active agent(s), prior to the onset of symptoms, particularly to a subject at risk of diseases or disorders provided herein. The terms encompass the inhibition or reduction of a symptom of the particular disease. Subjects with familial history of a disease in particular are candidates for preventive regimes in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

As used herein, and unless otherwise specified, a "prophylactically effective amount" of a compound is an amount sufficient to prevent a disease or disorder or prevent its recurrence. A prophylactically effective amount of a compound means an amount of therapeutic agent, alone or in combination with one or more other agent(s), that provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of a therapeutic agent, alone or in combination with one or more other agent(s), that provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein the term, and unless otherwise specified, an "Active Pharmaceutical Ingredient (API)" is any substance or mixture of substances intended to be used in the manufacture of a drug (medicinal) product and that, when used in the production of a drug, becomes an active ingredient of the drug product. Such substances are intended to affect the diagnosis, cure, mitigation, treatment, or prevention of disease or to affect the structure or function of the body.

As used herein, and unless otherwise specified, the term "Drug Product" is a finished dosage form, for example, an oral, nasal or transdermal formulation, that contains an active pharmaceutical ingredient, generally, but not necessarily in association with inactive ingredients.

The terms "composition," "formulation," and "dosage form," as used herein are intended to encompass compositions comprising the specified ingredient(s) (in the specified amounts, if indicated), as well as any product(s) that result, directly or indirectly, from combination of the specified ingredient(s) in the specified amount(s). By "pharmaceutical" or "pharmaceutically acceptable" it is meant that any diluent(s), excipient(s), absorption enhancer(s), or carrier(s) in the composition, formulation, or dosage form are compatible with the other ingredient(s) and not deleterious to the recipient thereof. Unless indicated otherwise, the terms "composition," "formulation," and "dosage form" are used herein interchangeably.

As used herein, the term "transdermal" relates to, being, or supplying a medication in a form for absorption through the skin into the bloodstream.

As used herein, the term "nasal" relates to, being or supplying a medication in a form for absorption through the nasal mucosa. Nasal delivery may be affected through a wide range of dosage forms including but not limited to solutions, gels, suspensions, emulsions, liposomes and microparticles.

As used herein "oral" relates to a medication in a form for absorption through the oral mucosal, sublingual, buccal, esophageal, gastric, or intestinal membranes. The term "capsule" refers to an oral composition in which the API and inactive ingredients are contained as a solid, liquid or semisolid within an outer shell comprised of gelatin, polymerized cellulose, or other suitable material. A capsule is intended to be swallowed wherein the composition will dissolve and release the API for systemic absorption through the esophageal, gastric, or intestinal lining.

The terms "tablet" and "wafer" includes spherical, round, oval, triangular, diamond, bullet, or oblong shaped oral compositions which contain the API, inactive ingredients, and optionally a saliva stimulant, which are formed with direct compression of a powdered formulation. Upon entry into the mouth, the compositions will dissolve and release the API for systemic absorption through the buccal, sublingual, esophageal, gastric, or intestinal lining.

The terms "strip" or "oral strip" includes square, rectangular, triangular, rounded, circular or oblong shaped oral compositions that contain the API, inactive ingredients, and optionally a saliva stimulant, that form a pliable matrix. Upon entry into the mouth, commonly placed under the tongue, the composition will dissolve and release the API for systemic absorption through the buccal, sublingual, esophageal, gastric, or intestinal lining.

As used herein "immediate release" is defined as the formulation of an active pharmaceutical ingredient(s) drug taken orally, nasally or transdermally that results in the rapid absorption of the drug into the blood after administration. Immediate release may be measured in vitro using the FDA Industry guidance on dissolution and/or permeability testing, or in vivo using blood plasma levels.

As used herein, "modified release" or "extended release" is defined as a formulation of an active pharmaceutical ingredient(s) taken orally, nasally or transdermally that releases the active pharmaceutical ingredients over several hours or days, to maintain a relatively constant plasma concentration of the drug. Such modifications may have a number of objectives, such as maintaining therapeutic activity for an extended time, reducing toxic effects, protecting the active substance against degradation due to low pH, targeting the active substance to a predefined segment of the gastrointestinal tract for local treatment or targeting active substance release at specified time-points. Modified release is measured by the appropriate FDA industry guidelines on modified release formulations.

The term "subject" is defined herein to include animals such as mammals, including, but not limited to, primates (e.g., humans), cows, sheep, goats, horses, dogs, cats, rabbits, rats, mice and the like. In specific embodiments, the subject is a human.

The terms "co-administration," "in combination with" and "in combination" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, or 4 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The term "psilocybin analogue" is defined herein to include any compound that is structurally related to psilocybin and functionally mimics and/or antagonizes the action of serotonin. Certain embodiments herein provide salts, cocrystals, solvates, isomers, hydrates, ions, zwitterions, complexes, prodrugs, precursors, metabolites, and/or other derivatives of the psilocybin. Certain embodiments herein provide mixtures of two or more of the psilocybin analogues provided herein. As described herein the psilocybin analogues are selected from the group consisting of the compounds as listed in Table (2) and salts and solvates thereof. Certain embodiments herein provide mixtures of two or more of the psilocybin analogues provided herein.

The psilocybin analogues described herein may be synthesized using any method known to one of ordinary skill in the art. Certain of the compounds are known to be able to be provided by application of biological processes to manufactured goods; the compounds are bioengineered.

The psilocybin analogues described herein may be provided by the alcohol or acid-base extraction of the psychoactive compounds from natural source that contain the compounds. The extraction methods are well known to those of skill in the art.

In certain embodiments the inventive formulation uses psilocybin and psilocybin analogues and combinations thereof, that may be derived synthetically or bioengineered; or extracted from naturally occurring mushrooms. Some of the manufacturing processes may be novel, as described herein, others may use techniques that have been well described in the art.

Provided herein are dosage forms, pharmaceutical formulations and compositions comprising an active pharmaceutical ingredient that is either (a) a novel indole of Structure (1), Structure (2), Structure (3), or (b) or a psilocybin analog. The dosage forms, pharmaceutical formulations and compositions release the active pharmaceutical ingredients into the bloodstream upon transdermal, nasal, or oral administration. In certain embodiments, the psilocybin analog is psilocin. In certain embodiments, the psilocybin analogue is 4-hydroxytryptophan. In certain embodiments, the psilocybin analogue is 4-hydroxytryptophol. In certain embodiments, the psilocybin analogue is 4-hydroxy-indole-3-acetaldehyde. In certain embodiments, the psilocybin analogue is 4-hydroxy-indole-3-acetic acid. In certain embodiments, the psilocybin analogue is norpsilocin. In certain embodiments, the psilocybin analogue is aeruginascin. In certain embodiments, the psilocybin analogue is baeocystin. In certain embodiment, the psilocybin analogue is norbaeocystin. In certain embodiments, the psilocybin analogue is 4-hydroxy-N-methyl-N-ethyltryptamine (4-OH-MET). In certain embodiment, the psilocybin analogue is 4-hydroxydiethyltryptamine (4-OH-DET). In certain embodiment, the psilocybin analogue is 4-hydroxy-N N-dipropyltryptamine (4-OH-DPT). In certain embodiments, the psilocybin analogue is 4-hydroxy-N,N-diisopropyltryptamine (4-OH-DiPT). In certain embodiments, the psilocybin analogue is N,N-dimethyltryptamine (DMT). In certain embodiments, the psilocybin analogue is indole-3-acetic acid. In certain embodiments, the psilocybin analogue is N,N-dimethyltryptamine-N-oxide (DMT-NO). In certain embodiments, the psilocybin analogue is lysergic acid diethylamide (LSD). In certain embodiments, the psilocybin analogue is O-acetylpsilocin (4-AcO-DMT). In certain embodiments, the psilocybin analogue is 5-methoxy-N,N-dimethyltryptamine (5-MeO-DMT). In certain embodiments, the psilocybin analogue is bufotenin (5-OH-DMT). In certain embodiments, the psilocybin analogue is ibogaine.

In certain embodiments, exemplary compounds have the structure as shown in Structure (1):

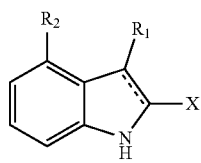

wherein:
X is H, $CF_3$, or a halogen that is selected from the group consisting of F, Cl, Br, I, or astatine; $R_1$ comprises an aliphatic substituent with a primary, secondary, tertiary, or quaternary amine; $R_2$ is hydrogen, hydroxyl, ester, ethers, aldehydes, acids, amides, thiols, sulfones, sulfonamides or combinations thereof.

In certain embodiments, the psilocybin analogues and combinations thereof, provided herein include any compound that is structurally related to psilocybin and functionally mimics and/or antagonizes the action of serotonin.

In certain embodiments, exemplary psilocybin analogues and combinations thereof, are the compounds provided in Table (2):

In certain embodiments, the pharmaceutical formulations and compositions comprising an active pharmaceutical ingredient that is either (a) an indole of the genus compound of the structures of Structure (1), (2), (3), (b) Table (1), (c) psilocybin analogues, or (d) Table (2) and combinations thereof, can be used in combination with other active agents.

In certain embodiments, the pharmaceutical formulations comprise MAOIs. MAOIs are drugs in a family of enzymes that catalyze the oxidation of monoamines, and certain psilocybin analogues and combinations thereof are known to be enzymatically degraded by MAOIs. The MAOIs, include but are not limited to harmala alkaloids, harmine, harmane, harmaline, hydrazine, iproniazid, isocarboxazid, nialamide, phenelzine, hydracarbazine, tranylcypromine, bifemelane, moclobemide, pirlindole, toloxatone, rasagiline, selegiline, safinamide, and other reversible inhibitors of monoamine oxidase A (RIMAs).

Certain embodiments herein encompass pharmaceutical formulations and compositions comprising an active pharmaceutical ingredient that is either (a) an indole of Structure (1) or (b) psilocybin analogues and combinations thereof, and optionally a monoamine oxidase inhibitor (also known as MAO inhibitors or MAOIs), wherein the formulations and compositions are prepared for transdermal administration.

Certain embodiments herein encompass pharmaceutical formulations and compositions comprising an active pharmaceutical ingredient that is either (a) an indole of Structure (1), Structure (2) or Structure (3), or (b) psilocybin analogues and combinations thereof, and optionally a monoamine oxidase inhibitor (also known as MAO inhibitors or MAOIs), wherein the formulations and compositions are prepared for oral administration. In certain embodiments, 5-HT antagonists can be used as an allosteric modulator or to improve therapeutic benefit of the psilocybin analogues. It is known that certain 5-HT antagonists can reduce pyschoactivity induced by the psilocybin analogues, which can be beneficial for treatment or to reduce side effects. Certain 5-HT antagonists include but are not limited to: ketanserin, clozapine, olanzapine, quetiapine, risperidone, asenapine, cyproheptadine, trazadone, mirtazapine, nefazodone, niaprazine, pizotifen, metergoline, or 2-bromo-LSD (BOL-148).

In certain embodiments, the pharmaceutical formulations and compositions comprising the active pharmaceutical ingredient of (a) an indole of Structure (1), Structure (2) or Structure (3), or (b) psilocybin analogues and combinations thereof are used for treating neurological, mood and abuse disorders. These formulations and compositions may be prepared for transdermal administration.

In certain embodiments, the pharmaceutical formulations and compositions comprising the active pharmaceutical ingredient of (a) an indole of the genus compound of the structures of Structure (1), (2), (3), (b) Table (1), (c) psilocybin analogues, or (d) Table (2) and combinations thereof are used for treating neurological, mood and abuse disorders. These formulations and compositions may be prepared for nasal administration.

In certain embodiments, the pharmaceutical formulations and compositions comprising the active pharmaceutical ingredient of ((a) an indole of the genus compound of the structures of Structure (1), (2), (3), (b) Table (1), (c) psilocybin analogues, or (d) Table (2) and combinations thereof are used for treating neurological, mood and abuse disorders. These formulations and compositions may be prepared for oral administration. Particular embodiments relate to the use an active pharmaceutical ingredient of (a) an indole of the genus compound of the structures of Structure (1), (2), (3), (b) Table (1) (c) psilocybin analogues, or (d) Table (2) and combinations thereof, for the preparation of pharmaceutical formulations and compositions for treating particular medical indications, as provided herein. The pharmaceutical formulations and compositions are intended for the transdermal delivery of the active pharmaceutical ingredient of (a) an indole of the genus compound of the structures of Structure (1), (2), (3), (b) Table (1), (c) psilocybin analogues, or (d) Table (2) and combinations thereof, in subjects in need thereof. Transdermal formulations can be manufactured in the form of sprayable liquids, gels, creams, lotions, ointments, and transdermal patches and are applied topically to the desired area.

Particular embodiments relate to the use an active pharmaceutical ingredient of (a) an indole of the genus compound of the structures of Structure (1), (2), (3), (b) Table (1), (c) psilocybin analogues, or (d) Table (2) and combinations thereof, for the preparation of pharmaceutical formulations and compositions for treating particular medical indications, as provided herein. The pharmaceutical formulations and compositions are intended for the oral delivery of the active pharmaceutical ingredient of (a) an indole of the genus compound of the structures of Structure (1), (2), (3), (b) Table (1), (c) psilocybin analogues, or (d) Table (2) and combinations thereof, in subjects in need thereof. Oral formulations can be manufactured in the form of tablets, capsules, softgels, strips, oral patch's and are intended for oral delivery to patient in need of therapy.

In certain embodiments the pharmaceutical formulations may be formulated for immediate release of the API. In certain embodiments the immediate release formulations are transdermal or nasal compositions In certain embodiments the pharmaceutical formulations may be formulated for immediate release of the API. In certain embodiments the immediate release formulations are oral compositions.

In certain embodiments the pharmaceutical formulations may be formulated for modified release of the API. In certain embodiments the immediate release formulations are transdermal compositions.

In certain embodiments the pharmaceutical formulations may be formulated for modified release of the API. In certain embodiments the immediate release formulations are oral compositions.

In certain embodiments, the transdermal composition comprises a transdermal patch or nasal formulation that delivers the active pharmaceutical ingredient across the skin or mucosal membrane into the bloodstream. In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for transdermal or nasal administration.

In certain embodiments, the formulations of an active pharmaceutical ingredient of (a) an indole of the genus compound of the structures of Structure (1), (2), (3), (b) Table (1), (c) psilocybin analogues, or (d) Table (2) and combinations thereof, effect an immediate release of the active pharmaceutical ingredient into the plasma upon transdermal, nasal or oral administration. In particular embodiments, the formulations comprising an active pharmaceutical ingredient of (a) an indole of the genus compound of the structures of Structure (1), (2), (3), (b) Table (1), (c) psilocybin analogues, or (d) Table (2) and combinations thereof, comprise a therapeutically or prophylactically effective amount of the active pharmaceutical ingredient, and, optionally, one or more excipients.

In certain embodiments of the inventive transdermal, nasal, or oral formulation use psilocybin and psilocybin analogues and combinations thereof, that may be derived synthetically or bioengineered; or extracted from naturally occurring mushrooms that have been well described in the art.

In certain embodiments of the inventive transdermal, nasal or oral formulation use psilocybin and psilocybin analogues and combinations thereof, that may be derived synthetically or bioengineered; or extracted from naturally occurring mushrooms using novel chemical synthesis or extraction techniques as described herein.

In certain embodiments the transdermal pharmaceutical dosage composition is in the form of sprayable liquids, gels, creams, lotions, ointments and transdermal patches, wherein the active pharmaceutical ingredient is infused with inactive ingredients that enhance the delivery properties of the composition and stabilize the active pharmaceutical ingredient. In one embodiment, penetration enhancers may be an inactive ingredient. The penetration enhancers may include fatty acids and oils that may be, but are not limited to: castor oil, coconut oil, medium chain triglycerides (MCT), jojoba oil, sunflower oil, argan oil, almond oil, olive oil, mineral oil, petroleum jelly, cocoa butter, shea butter, or other esters, triglycerides, or functional derivatives thereof.

In certain embodiments, the surfactants may be used in the transdermal delivery system as emulsifiers and stabilizers can encapsulate drugs for better stability and permeability properties. Surfactants include but are not limited to: polysorbates (e.g. Tween, polysorbate 20), sorbitans (Span), phospholipids (lecithin), lauryl sulfates, betaines, propionates, fatty alcohols and alkanolamides, fatty acid esters, amine oxides, myristates, and azones.

In certain embodiments, co-solvents may be used in the transdermal formulation to improve drug solubility and permeability, while acting as a humectant for better skin feel. Common co-solvents include but are not limited to: alcohols such as ethanol, isopropanol, glycerin, propylene glycol, dipropylene glycol, polyethylene glycol, diethylene monoethyl ether, Cremophores, siloxanes, polyethylenes, and water.

In certain embodiments, thickeners may be used in the transdermal formulation to reduce separation and provide a suitable matrix for modified delivery. Common thickeners include but are not limited to: acrylates, carbomers, cellulose matrices, silicones, carrageenans, gums, resins, polysaccharides, and high melting point waxes and oils such as beeswax, coconut oil, palm oil, soybean oil, stearic acid, rapeseed, cocoa butter, shea butter, gums, rosins, resins, paraffins, and petroleum jelly.

In certain embodiments, tackifiers may be used in the transdermal formulation to increase adhesion for extended wearability. Common tackifiers include but are not limited to gums, resins (natural or modified), carbomers, or other natural or synthetic polymers.

In certain embodiments, preservatives may be used in the transdermal formulation to improve formulation stability and retard microbial growth. Common preservatives include but are not limited to: parabens, sorbates, benzoates, silicas, chlorides, phenols, chlorhexidine, citric acid, triclosan, Vitamin E (or tocopherols), chelators, metals, salts, and alcohols. Lastly the formulation is typically emulsified with a hydrophilic ingredient such as water, or *Aloe barbadensis* juice.

In certain embodiments, the formulations comprising an active pharmaceutical ingredient of (a) an indole of Structure (1) or (b) psilocybin analogues and combinations thereof effect a controlled release of the active pharmaceutical ingredient transdermally upon administration. In certain embodiments, the formulations comprising the active pharmaceutical ingredient, comprise a therapeutically or prophylactically effective amount of the active pharmaceutical ingredient(s) and a drug release controlling component that is capable of controlled and sustained release of the active pharmaceutical ingredients directly into the bloodstream.

In certain embodiments, the transdermal dosage form is a transdermal delivery device. Any device conventional in the art for transdermally delivering a therapeutic agent to a patient can be used for the transdermal delivery of the compositions of the invention and as the transdermal delivery device. For example, the transdermal delivery device can be a reservoir-type transdermal delivery device, a polymer-matrix type transdermal delivery device, or a drug-in-adhesive type transdermal delivery device or a multilaminate type transdermal delivery device. The transdermal delivery device is designed so that when contacted with the patient's skin, the active pharmaceutical ingredient of the present invention is delivered in a therapeutically effective amount In certain embodiments, the transdermal delivery device is of the drug-in-adhesive type device comprising the active pharmaceutical ingredient dispersed directly in a pressure-sensitive adhesive matrix. The adhesive matrix is preferably supported on the topside with an impermeable backing film and on the side that faces the skin with an impermeable release liner. To administer the active pharmaceutical ingredient, the release liner is removed to expose the adhesive matrix, and the device is contacted with the skin. The adhesive matrix functions to adhere the device to the skin and, typically, to control the delivery rate of the active pharmaceutical ingredient. Similar to the polymer-matrix design, the drug-in-adhesive design allows the active pharmaceutical ingredient to diffuse out of the adhesive matrix, contact the patient's skin, and penetrate the skin. The delivery rate of the active pharmaceutical ingredient is usually determined by the rate of diffusion of the active pharmaceutical ingredient(s) out of the adhesive matrix. Multiple drug-in-adhesive layers can be laminated together between rate-controlling membranes for longer, extended delivery. The delivery rate is such that effective amount of the active pharmaceutical ingredient is delivered to the patient in need of the active pharmaceutical ingredient.

In certain embodiments, a reservoir-type transdermal delivery device preferably comprises a reservoir, usually a liquid, or semisolid located between an impermeable backing film and a rate-controlling membrane that is covered with a pressure-sensitive adhesive skin-contacting layer. The reservoir, which may be a solution or a dispersion, contains the composition of the invention. The transdermal delivery device is preferably supported by the impermeable backing film and the adhesive surface is protected by a release liner, To administer the active pharmaceutical ingredient of the present invention, the release liner is removed to expose the pressure-sensitive adhesive and the pressure-sensitive adhesive is contacted with the skin. The active pharmaceutical ingredient of the present invention is permeable through the rate-controlling membrane, and penetrates through it and the adhesive, contacts the skin, and then penetrates the skin. The delivery rate of the active pharmaceutical invention is usually determined by the rate that the active pharmaceutical ingredient penetrates the rate-controlling membrane, In certain embodiments, the transdermal delivery device is of the polymer-matrix design. In the polymer-matrix design, the psilocybin analog and combinations thereof, are dispersed in a polymer matrix that controls the delivery rate of the active pharmaceutical ingredient. Preferably the polymer-matrix reservoir is supported on an impermeable backing layer. An adhesive layer is attached to the surface of the polymer matrix. To administer the active pharmaceutical ingredients the release liner is removed to expose the polymer matrix and the ring of pressure-sensitive adhesive, and the device is contacted with the skin. The adhesive holds the device against the skin so that the polymer matrix directly contacts the skin. When the polymer matrix is contacted with the skin, the active pharmaceutical ingredient (s) diffuse out of the polymer matrix, contacts the patient's skin, and penetrates the skin. The delivery rate of the active pharmaceutical ingredients is usually determined by the rate of diffusion active pharmaceutical ingredient out of the polymer matrix.

Adhesives comprise cross-linking monomeric units or sites can be incorporated into the adhesive polymers. For example, cross-linking monomers can be incorporated into polyacrylate polymers. The cross-linking monomers may, for example, provide sites for cross-linking the polymer matrix after dispersing the psilocybin analog and combinations thereof, into the polymer. Known adhesives comprise cross-linking monomers for polyacrylate polymers include, for example, polymethacrylic esters of polyols such as butylene diacrylate, butylene dimethacrylate and trimethylol propane trimethacrylate, polyisobutylene type adhesives and silicone. Other monomers that provide cross-linking sites include allyl acrylate, allyl methacrylate, diallyl maleate, silyl ethers, and silanes. Monomers are then polymerized using methods known by those skilled in the art to comprise polyacrylate (acrylics), polysiloxane (silicones), or polyisobutylene (or other rubber) adhesive matrices containing cross-linkers, functional groups, or vinyl acetate to suspend, stabilize, and release the active pharmaceutical ingredient.

In an embodiment of the present invention, the transdermal delivery device may optionally include one or more penetration enhancers, which increase the rate at which the active pharmaceutical ingredients penetrate through the patient's skin. Preferably, the penetration enhancer penetrates the rate-controlling membrane or diffuses out of the polymer matrix or adhesive matrix so that it can contact the patient's skin and improve penetration of active pharmaceutical ingredient as defined herein through the patient's skin. Suitable penetration enhancers for use in the transdermal delivery devices and compositions of the invention include, for example, $C_{2-4}$ alcohols, e.g., ethanol and isopropanol, polyethylene glycol monolaurate, polyethylene glycol-3-lauramide, dimethyl lauramide, polysorbates, sorbitans, fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene. In certain embodiments, the transdermal patches as described herein are used co-administered with penetration enhancers. In certain embodiments, the penetration enhancers may include oils that may be, but are not limited to: castor oil, coconut oil, medium chain triglycerides (MCT), jojoba oil, sunflower oil, argan oil, almond oil, olive oil, mineral oil, petroleum jelly, cocoa butter, and shea butter. Other penetration enhancers for use in transdermal patches include, for example, $C_{2-4}$ alcohols, e.g., ethanol and isopropanol, polyethylene glycol monolaurate, polyethylene glycol-3-lauramide, dimethyl lauramide, polysorbates (Tween), sorbitans (Span), fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene.

In certain embodiments, the delivery rate of the active pharmaceutical ingredient may be delivered in a once a day transdermal patch application. In certain embodiments, the delivery rate of the API may be delivered over the course of 6-12 hours. In certain embodiments, the delivery rate of the API may be delivered over 12-24 hours. In certain embodiments the delivery rate of the API may be delivered over 24-48 hours. In other embodiments, the transdermal patch may be applied once every 2 days; once every 3 days; once every 4 days; once every 5 days; once every 5 days; or once every 7 days. The transdermal patch delivery rate options will facilitate patient dosing compliance while delivering a steady-state systemic safe and effective drug concentrations.

As described herein, certain embodiments provide transdermal formulations of active pharmaceutical ingredient as described herein, useful in methods relating to differing dosage amounts and/or dosage periods; providing alternative pharmacokinetic profiles, pharmacodynamic profiles, and/or safety profiles; permitting long term maintenance therapies; providing for the testing of new indications for the psilocybin analogues; and other potential advantageous benefits. In particular embodiments, formulations provided herein (e.g. sprayable liquids, gels, creams, lotions, ointments, or transdermal patch for the dermal delivery of the active pharmaceutical ingredient) comprise the active pharmaceutical ingredients ((a) an indole of the genus compound of the structures of Structure (1), (2), (3), (b) Table (1), (c) psilocybin analogues, or (d) Table (2) alone or in combination) in a specific pharmaceutically active amount. In particular embodiments, the specific amount of the active pharmaceutical ingredient as disclosed herein, in the formulation is, e.g. about 1 mg, about 2 mg, about 3 mg, about 4 mg, about 5 mg, about 6 mg, about 7 mg, about 8 mg, least about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg about 23 mg, about 24 mg, about 25 mg, about 26 mg, about 27 mg, about 28 mg, about 29 mg, about 30 mg, about 31 mg about 32 mg, about 33 mg, about 34 mg, about 35 mg about 36 mg, about 37 mg, about 38 mg, about 39, about 40 mg, about 45 mg, about 50 mg, about 55 mg, about 60 mg, about 65 mg, about 70 mg, about 75 mg, about 80 mg, about 85 mg, about 90 mg, about 95 mg, or at least 100 mg. In particular embodiments, the specific amount of the psilocybin analogue in the formulation is, e.g., at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least 40 mg, at least 45 mg, at least 50 mg, at least about 55 mg, at least about 60 mg, at least about 65 mg, at least about 70 mg, at least about 75 mg, at least about 80 mg, at least about 85 mg, at least about 90 mg, at least about 95 mg, or at least 100 mg.

In more particular embodiments, the specific amount of the active pharmaceutical ingredient as disclosed herein, in the formulation is, e.g. about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg about 23 mg, about 24 mg, about 25 mg, about 30 mg, about 35 mg, about 40 mg, about 45 mg, about 50 mg, about 55 mg about 60 mg, about 65 mg, about 70 mg, about 75 mg about 80 mg, about 85 mg, about 90 mg, or at least 100 mg.

In more particular embodiments, the specific amount of the active pharmaceutical ingredient in the formulation is, e.g., at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, or at least 100 mg.

In a particular embodiment the active pharmaceutical ingredient in the pharmaceutical formulation is from about 5 mg to 100 mg, or from about 5 mg to 25 mg, or from about 25 mg to 50 mg, or from about 50 mg to 75 mg, or from about 75 mg to 100 mg.

As described herein, certain embodiments provide transdermal formulations of active pharmaceutical ingredient as described herein, relating to the skin application size for transdermal delivery devices. Application area is a crucial metric for determining drug fluxes, to differ dosage, and to provide sufficient area for efficient transdermal delivery. In particular embodiments the API (compounds of (a) an indole of the genus compound of the structures of Structure (1), (2), (3), (b) Table (1), (c) psilocybin analogues, or (d) Table (2) (alone or in combination) is contained within a drug delivery device (e.g. sprayable liquids, gels, creams, lotions, ointments, or transdermal patch) and is applied to the skin of a human or mammal in an area of not more than 1 cm, or at least 2 $cm^2$, at least 3 $cm^2$, at least 4 $cm^2$, at least 5 $cm^2$, at least 6 $cm^2$, at least 7 $cm^2$, at least 8 $cm^2$, at least 9 $cm^2$, at least 10 $cm^2$, at least 15 $cm^2$, at least 20 $cm^2$, at least 25 $cm^2$, at least 30 $cm^2$, at least 35 $cm^2$, at least 40 $cm^2$, at least 45 $cm^2$, at least 50 $cm^2$, at least 60 $cm^2$, at least 70 $cm^2$, at least 80 $cm^2$, at least 90 $cm^2$, or at least 100 $cm^2$ at least 150 $cm^2$, at least 200 $cm^2$, at least 250 $cm^2$, at least 300 $cm^2$, at least 350 $cm^2$, at least 400 $cm^2$, at least 450 $cm^2$, at least 500 $cm^2$, at least 600 $cm^2$, at least 700 $cm^2$, at least 800 $cm^2$, at least 900 $cm^2$, or at least 1000 $cm^2$.

In particular embodiments the API alone or in combination, is contained within a drug delivery device (e.g. sprayable liquids, gels, creams, lotions, ointments, or transdermal patch) and is applied to the skin of a human or mammal in an area of not more than 1 cm, or at least 2 $cm^2$, at least 3 $cm^2$, at least 4 $cm^2$, at least 5 $cm^2$, at least 6 $cm^2$, at least 7 $cm^2$, at least 8 $cm^2$, at least 9 $cm^2$, at least 10 $cm^2$, at least 15 cm², at least 20 cm², at least 25 cm², at least 30 cm², at least 35 cm², at least 40 cm², at least 45 cm², at least 50 cm², at least 60 cm², at least 70 cm², at least 80 cm², at least 90 cm², or at least 100 cm².

In an embodiment the API alone or in combination is applied to the skin of a human or mammal in an area from about 1 cm² to 10 cm², from about 10 cm² to 40 cm², from about 40 cm² to 100 cm², or more preferably 5 cm² to 40 cm².

In certain embodiments the active pharmaceutical ingredients are delivered in an oral pharmaceutical formulation composition comprising a capsule or tablet that delivers the API into the bloodstream through the esophageal, gastric, and/or intestinal membranes.

In certain embodiments the oral composition is swallowed and the active pharmaceutical ingredients are further delivered into the bloodstream through the esophageal, gastric, and/or intestinal membranes In certain embodiments the oral composition comprises a tablet, wafer, or strip that delivers the active pharmaceutical ingredient into the bloodstream through the sublingual, buccal, or other oral mucosal membrane.

In certain embodiments the oral composition comprises an oral patch or oral film that delivers the active pharmaceutical ingredient into the bloodstream through the sublingual, buccal, or other oral mucosal membrane.

In certain embodiments the oral composition is swallowed, and the active pharmaceutical ingredients are further delivered into the bloodstream through the esophageal, gastric, and/or intestinal membranes.

In certain embodiments the oral composition comprises a powder, solution, or suspension that delivers the active pharmaceutical ingredient into the bloodstream through the sublingual, buccal, or other oral mucosal membrane.

In certain embodiments the oral composition is swallowed, and the active pharmaceutical ingredients are further delivered into the bloodstream through the esophageal, gastric, and/or intestinal membranes.

In certain embodiments, the formulations of active pharmaceutical ingredient of (a) an indole of the genus compound of the structures of Structure (1), (2), (3), (b) Table (1), (c) psilocybin analogues, or (d) Table (2) and combinations thereof, effect an immediate release of the active pharmaceutical ingredient into the plasma upon oral administration. In particular embodiments, the formulations comprising an active pharmaceutical ingredient of (a) an indole of the genus compound of the structures of Structure (1), (2), (3), (b) Table (1) (c) psilocybin analogues, or (d) Table (2) and combinations thereof, comprise a therapeutically or prophylactically effective amount of the active pharmaceutical ingredient, and, optionally, one or more excipients.

In certain embodiments, the formulations of active pharmaceutical ingredient of (a) an indole of (a) an indole of the genus compound of the structures of Structure (1), (2), (3), (b) Table (1), (c) psilocybin analogues, or (d) Table (2) and combinations thereof, effect a modified release of the active pharmaceutical ingredient into the plasma upon oral administration. In particular embodiments, the formulations comprising an active pharmaceutical ingredient of (a) an indole of the genus compound of the structures of Structure (1), (2), (3), (b) Table (1), (c) psilocybin analogues, or (d) Table (2) and combinations thereof, comprise a therapeutically or prophylactically effective amount of the active pharmaceutical ingredient, and, optionally, one or more excipients.

In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for oral administration.

In certain embodiments, the embodiments herein encompass the use of an active pharmaceutical ingredient of (a) an indole of the genus compound of the structures of Structure (1), (2), (3), (b) Table (1), (c) psilocybin analogues, or (d) Table (2) and combinations thereof, for the preparation of a pharmaceutical composition for treating neurological, mood and abuse disorders, wherein the composition is prepared for oral administration.

In certain embodiments the oral composition contains inactive ingredients that enhance drug delivery properties and stabilize the active ingredient.

In one embodiment fillers may be included as an inactive ingredient. The fillers can act as matrix to affect the dissolution time or act as binders to improve tablet stability. The fillers may include but are not limited to: starch, citric acid, tartaric acid, bicarbonates, phosphates, polyvinyl pyrrolidone, cellulose (natural and modified), croscarmellose, glycolates, acrylates, acetates, gelatin, gums, alginates, pectin, chitosan, chitin, salts, polysaccharides, mucilages, sugars, sucrose, lactose, and dextrose.

In another embodiment, lubricants may be included as an inactive ingredient. The lubricants act to improve powder flowability or reduce friction on manufacturing parts; these may include but are not limited to: magnesium stearate, talc, stearic acid, and silicon dioxide.

In yet another embodiment, flavorings may be included as an inactive ingredient. The flavorings can mask the taste of bitter agents or improve the taste of the oral composition; these include but are not limited to: sugars, dextrose, sucrose, sucralose, *stevia*, essential oils, citric acid, and natural or artificial flavorings. Optionally, coloring agents can be included in the powders to improve visual properties or to differentiate product offerings; these coloring agents can be natural or artificial dyes, pigments, chelates, or metals.

In certain embodiments the oral composition contains surfactants that are emulsifiers and stabilizers that can encapsulate drugs for better stability, taste, permeability, and drug release properties. Surfactants include but are not limited to vegetable oils, triglycerides, esters, polysorbates (Tween), sorbitans (Span), phospholipids (e.g. lecithin), lauryl sulfates, betaines, propionates, fatty acids, fatty alcohols, saponins and alkanolamides, amine oxides, cyclodextrins, myristates and azones.

In certain embodiments the oral composition contains co-solvents to improve drug solubility, dissolution, and permeability. Co-solvents include but are not limited to: alcohols such as ethanol, isopropanol, glycerin, propylene glycol, dipropylene glycol, polyethylene glycol, diethylene monoethyl ether, Cremophores, siloxanes, polyethylenes, and water.

In certain embodiments the oral composition contains thickeners to reduce dissolution and provide a suitable matrix for delivery. Thickeners include but are not limited to: acrylates, carbomers, cellulose matrices, silicones, carrageenans, polysaccharides, and high melting point waxes and oils such as beeswax, coconut oil, palm oil, soybean oil, stearic acid, rapeseed, cocoa butter, shea butter, gums, rosins, resins, paraffins, and petroleum jelly.

In certain embodiments the oral composition contains preservatives to improve formulation stability and retard microbial growth. Preservatives include but are not limited to: parabens, sorbates, benzoates, silicas, chlorides, phenols, chlorhexidine, citric acid, triclosan, Vitamin E (or tocopherols), chelators, metals, salts, and alcohols.

In certain embodiments the oral composition contains enteric coatings to modify and extend release within the gastrointestinal tract. Enteric coatings include high melting point waxes, fatty acids, sugars, fibers, and polymers and others.

In another embodiment the oral composition contains inactive ingredients that change the physical properties of the drug delivery system such as pH, solubility, dissolution, hydrophobicity, and stability. Many such compounds are known to those of skill in the art.

In certain embodiments the oral composition contains membrane penetration enhancers to increase systemic delivery. Suitable penetration enhancers for use in the oral composition include, for example, $C_{2-4}$ alcohols, e.g. ethanol and isopropanol, polyethylene glycol monolaurate, polyethylene glycol-3-lauramide, dimethyl lauramide, sorbitans (Span), polysorbates (e.g. Tween, polysorbate 20), fatty acids, esters of fatty acids having from about 10 to about 20 carbon atoms, monoglycerides or mixtures of monoglycerides of fatty acids having a total monoesters content of at least 51% where the monoesters are those with from 10 to 20 carbon atoms, and mixtures of mono-, di- and tri-glycerides of fatty acids. Suitable fatty acids include, for example, lauric acid, myristic acid, stearic acid, oleic acid, linoleic acid and palmitic acid. Monoglyceride permeation enhancers include, for instance, glycerol monooleate, glycerol monolaurate, and glycerol monolinoleate. Terpenes and terpenoids are derived from natural isoprene biosynthesis and can also be utilized to disrupt the skin membrane and increase API permeability. Terpenes and terpenoids are derived from natural isoprene biosynthesis and can also be utilized to disrupt the skin membrane and increase API permeability. Examples of terpenes include but are not limited to: menthol, menthone, camphor, nerolidol, limonene, myrcene, anethole, eugenol, 1,8-cineole, terpinolene, pinene, and humulene.

In certain embodiments the active pharmaceutical ingredient of (a) an indole of (a) an indole of the genus compound of the structures of Structure (1), (2), (3), (b) Table (1), (c) psilocybin analogues, or (d) Table (2) and combinations thereof is included in at least one matrix of the oral composition. In another embodiment active pharmaceutical ingredient of ((a) an indole of the genus compound of the structures of Structure (1), (2), (3), (b) Table (1), (c) psilocybin analogues, or (d) Table (2) and combinations thereof is included in at least two matrices of the oral composition. In another embodiment the active pharmaceutical ingredient of (a) an indole of the genus compound of the structures of Structure (1), (2), (3), (b) Table (1), (c) psilocybin analogues, or (d) Table (1) and combinations thereof is included in at least three matrices of the oral composition. In another embodiment the active pharmaceutical ingredient of (a) an indole of (a) an indole of the genus compound of Structure (1), (2), (3), (b) Table (1), (c) psilocybin analogues, or (d) Table (2) and combinations thereof is included in at least four matrices of the oral composition. In yet another embodiment the active pharmaceutical ingredient of (a) an indole of the genus compound of Structure (1), (2), (3), (b) Table (1), (c) psilocybin analogues, or (d) Table (2) and combinations thereof is included in at least five matrices of the oral composition.

In certain embodiments the active pharmaceutical ingredients are single active ingredients. In a preferred embodiment the compounds of (a) an indole of the genus compound of the structures of Structure (1), (2), (3), (b) Table (1), (c) psilocybin analogues, or (d) Table (2) are orally administered in a capsule. In a preferred embodiment the compounds of (a) an indole of the genus compound of Structure (1), (2), (3), (b) Table 1, (c) psilocybin analogues, or (d) Table (2) are orally administered in a tablet. In a preferred embodiment the compounds of (a) an indole of the genus compound of the structures of Structure (1), (2), (3), (b) Table (1), (c) psilocybin analogues, or (d) Table (2) are orally administered in a wafer. In a preferred embodiment the compounds of (a) an indole of the genus compound of the structures of Structure (1), (2), (3), (b) Table (1), (c) psilocybin analogues, or (d) Table (2) is orally administered in a strip. In a preferred embodiment the compounds of (a) an indole of the genus compound of Structure (1), (2), (3), (b) Table (1), (c) psilocybin analogues, or (d) Table (2) is orally administered in a transdermal patch. In a preferred embodiment the compound of (a) an indole of the genus compound of the structures of Structure (1), (2), (3), (b) Table (1), (c) psilocybin analogues, or (d) Table (2) is orally administered in a powder. In a preferred embodiment the compounds of (a) an indole of the genus compound of the structures of Structure (1), (2), (3), (b) Table (1), (c) psilocybin analogues, or (d) Table (2) is orally administered in a suspension. In a preferred embodiment the compounds of (a) an indole of the genus compound of the structures of Structure (1), (2), (3), (b) Table (1), (c) psilocybin analogues, or (d) Table (2) is orally administered in a solution.

In another embodiment mixtures of psilocybin analogues are delivered in the same oral composition as described herein. In a preferred embodiment the compounds of (a) an indole of the genus compound of the structures of Structure (1), (2), (3), (b) Table (1), (c) psilocybin analogues, or (d) Table (2) is orally administered either singularly or in combination with other (a) an indole of the genus compound of the structures of Structure (1), (2), (3), (b) Table (1), (c) psilocybin analogues, or (d) Table (2) in an oral composition as described herein.

In certain embodiments the oral composition contains at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 60 mg, at least 70 mg, at least 80 mg, at least 90 mg, at least 100 mg, at least 120 mg, at least 140 mg, at least 160 mg, at least 180 mg, at least 200 mg, at least 250 mg, at least 300 mg, at least 350 mg, at least 400 mg, at least 450 mg, and/or at least 500 mg of the active pharmaceutical ingredient of (a) an indole of the genus compound of the structures of Structure (1), (2), (3), (b) Table (1), (c) psilocybin analogues, or (d) Table (2) and combinations thereof.

In certain embodiments the systemic drug release of the oral composition containing the active pharmaceutical ingredient of (a) an indole of the genus compound of the structures of Structure (1), (2), (3), (b) Table (1), (c) psilocybin analogues, or (d) Table (2) and combinations thereof occurs with therapeutically active onset of not more than 1 minute, not more than 3 minutes, not more than 5 minutes, not more than 7 minutes, not more than 9 minutes, not more than 11 minutes, not more than 13 minutes, not more than 15 minutes, not more than 17 minutes, not more than 19 minutes, not more than 21 minutes, not more than 23 minutes, not more than 25 minutes, not more than 27 minutes, not more than 30 minutes, not more than 45 minutes, not more than 60 minutes, not more than 90 minutes, not more than 120 minutes, not more than 150 minutes, and not more than 180 minutes.

In certain embodiments the duration of the therapeutic or prophylactic effect of the oral composition containing the active pharmaceutical ingredient of (a) an indole of the genus compound of the structures of Structure (1), (2), (3), (b) Table (1), (c) psilocybin analogues, or (d) Table (2) and combinations thereof sustains for at least 5 minutes, at least 15 minutes, at least 30 minutes, at least 45 minutes, at least 60 minutes, at least 90 minutes, at least 120 minutes, at least 3 hours, at least 4 hours, at least 5 hours, at least 6 hours, at least 8 hours, at least 10 hours, at least 12 hours, at least 18 hours, at least 1 day, at least 2 days, at least 3 days, at least 4 days, at least 5 days, at least 6 days, and at least 1 week.

As described herein, certain embodiments provide oral compositions of active pharmaceutical ingredient as described herein, useful in methods relating to differing dosage amounts and/or dosage periods; providing alternative pharmacokinetic profiles, pharmacodynamic profiles, and/or safety profiles; permitting long term maintenance therapies; providing for the testing of new indications for the psilocybin analogues; and other potential advantageous benefits.

Provided herein are methods of preventing, managing, and treating neurological, mood or addictive disorders including post-treatment Lyme disease syndrome, dementias, Alzheimer's disease, post-traumatic stress disorder, anorexia nervosa, depression, anxiety, addiction, substance abuse including but not limited to opioid addiction, alcohol addiction, nicotine addiction, cannabinoid addiction, headache, central nervous system inflammation, dementia, cognition and memory by administering psilocybin analogues transdermally, intranasally, or orally.

In certain embodiment the active pharmaceutical ingredients are single active pharmaceutical ingredients. In a preferred embodiment, the compounds of (a) an indole of the genus compound of the structures of Formula (1), (2), (3), (b) Table (1), (c) psilocybin analogues, or (d) Table (2) delivered in a transdermal patch delivery system. In a preferred embodiment, the active pharmaceutical ingredient is transdermally delivered in a transdermal patch delivery system.

In another embodiment, mixtures of psilocybin analogues are delivered in the same transdermal delivery system. In a preferred embodiment the psilocybin analogue is transdermally delivered either singularly or in combination with other psilocybin analogues in a transdermal patch delivery system.

In another embodiment, the active pharmaceutical ingredients thereof are co-administered with one or more therapeutic agent. The co-administered agent may be MAOI. In another embodiment, a compound from another class of neurologically active agents is co-administered providing for a synergistic therapeutic effect is. Other neurologically active agents include those compounds that fall into the following classes of compounds: antipsychotics, antidepressants, anxiolytics, stimulants, reuptake inhibitors (SSRI or SSNRI), monoamine oxidase inhibitors (MAOI), cognitive-enhancing agents, tricyclic antidepressants, mood stabilizers, NMDA antagonists and 5-HT antagonists.

In yet another embodiment, the (a) an indole of the genus compound of the structures of Structure (1), (2), (3), (b) Table (1), (c) psilocybin analogues, or (d) Table (2), either singularly or in mixtures, are co-administered with one or more therapeutic agents to reduce substance abuse. For the treatment of opioid addiction, other co-administered compounds can include: methadone, buprenorphine, naloxone, naltrexone, and the like. For the treatment of alcoholism, other co-administered compounds can include ethyl alcohol, disulfiram, naltrexone, acamprosate, benzodiazepines, and the like. For the treatment of nicotine addiction, other co-administered compounds can include low dose nicotine, Bupropion, Varenicline and the like.

Provided herein are methods of preventing, managing, treating neurological, mood or addictive disorders including post-treatment Lyme disease syndrome, dementias, Alzheimer's disease, post-traumatic stress disorder, anorexia nervosa, depression, anxiety, addiction, substance abuse including but not limited to opioid addiction, alcohol addiction, nicotine addiction, cannabinoid addiction, headache, central nervous system inflammation, dementia, cognition and memory by administering psilocybin analogues transdermally.

EXAMPLES

Example 1

Purified N, N-dimethyltryptamine (DMT1.8% w/w, wet) was dissolved with a combination of ethyl acetate (7.2% w/w, wet) and ethanol (7.2% w/w, wet) and incorporated into a Duro-Tak 4098 acrylate adhesive (83.8% w/w, wet) and mixed thoroughly. The mixture was formulated to a 150 µm thickness onto the siliconized side of a Scotchpak 9709 release liner. The formulation was dried at 75° C. and laminated onto an occlusive Scotchpak 9733 polyester backing before cutting transdermal patches to a size of 10 cm². The final transdermal patches were stored within a heat-sealed aluminized pouch to reduce oxidation.

Linear drug release (n=3 transdermal patches) was observed over 72 hours with over 80% DMT released at 72 hours (FIG. 1). Average DMT flux was quantified at 37 ug/cm²*hr over 72 hours.

Example 2

Purified DMT (2.0% w/w, wet) was dissolved in ethanol (8.0% w/w, wet) and incorporated into Duro-Tak 4098 adhesive (90.0% w/w, wet) and mixed thoroughly. The mixture was formulated to a 250 µm thickness onto a release liner. The formulation was dried and laminated onto an occlusive backing before cutting transdermal patches to a size of 10 cm². The final transdermal patches (6.4% w/w DMT) were stored within a heat-sealed aluminized pouch to reduce oxidation. Average DMT flux was quantified at 43 µg/cm²*hr over 72 hours

Example 3

Purified DMT (2.0% w/w, wet) was dissolved in ethanol (8.1% w/w, wet) and incorporated into silicone adhesives Bio PSA 7-4302 (44.9% w/w, wet) and Bio PSA 7-4202 (44.9% w/w, wet) and mixed thoroughly. The mixture was formulated to a 150 µm thickness onto a release liner. The formulation was dried and laminated onto an occlusive backing before cutting transdermal patches to a size of 10 cm². The final transdermal patches (3.9% w/w DMT) were stored within a heat-sealed aluminized pouch to reduce oxidation. Average DMT flux was quantified at 31 µg/cm²*hr over 48 hours.

Example 4

Purified DMT (2.0% w/w, wet) was dissolved in ethanol (4.0% w/w, wet) and incorporated into a Duro-Tak 6908 polyisobutylene adhesive (94.0% w/w, wet) and mixed thoroughly. The mixture was formulated to a 150 μm thickness onto a release liner. The formulation was dried and laminated onto an occlusive backing before cutting transdermal patches to a size of 10 cm². The final transdermal patches (5.4% w/w DMT) were stored within a heat-sealed aluminized pouch to reduce oxidation. Average DMT flux was quantified at 7 μg/cm²*hr over 30 hours.

Example 5

Purified DMT (3.8% w/w, wet) was dissolved in ethanol (15.9% w/w, wet) and incorporated into Duro-Tak 4098 adhesive (80.3% w/w, wet) and mixed thoroughly. The mixture was formulated to a 200 μm thickness onto a release liner. The formulation was dried and laminated onto an occlusive backing before cutting transdermal patches to a size of 10 cm². The final transdermal patches (10.9% w/w DMT) were stored within a heat-sealed aluminized pouch to reduce oxidation. Average DMT flux was quantified at 57 μg/cm²*hr over 48 hours.

Example 6

Purified DMT (4.2% w/w, wet) was dissolved in ethanol (11.2% w/w, wet) and incorporated into a Duro-Tak 4098 acrylate adhesive (77.5% w/w, wet) before isopropyl myristate (7.1% w/w, wet) was added and mixed thoroughly. The mixture was formulated to a 200 μm thickness onto a release liner. The formulation was dried and laminated onto an occlusive backing before cutting transdermal patches to a size of 10 cm². The final transdermal patches (10.3% w/w DMT) were stored within a heat-sealed aluminized pouch to reduce oxidation. Average DMT flux was quantified at 145 μg/cm²*hr over 48 hours.

Example 7

Purified 4-acetoxy-N, N-dimethyltryptamine (4-AcO-DMT, 3.2% w/w, wet) was dissolved in ethanol (12.4% w/w, wet) and incorporated into a Duro-Tak 4098 acrylate adhesive (84.4 w/w, wet) and mixed thoroughly. The mixture was formulated to a 200 μm thickness onto the siliconized side of a release liner. The formulation was dried and laminated onto an occlusive polyester backing before cutting transdermal patches to a size of 10 cm². The final transdermal patches (9.0% w/w 4-AcO-DMT) were stored within a heat-sealed aluminized pouch to reduce oxidation. Average 4-AcO-DMT flux was quantified at 98 μg/cm²*hr over 48 hours.

Example 8

A second DIA with excipients listed above will be cast directly onto the backing and laminated onto a rate-controlling membrane. The DIA-coated liner from Example 1 will then be laminated to the backing/DIA/membrane material to form a multi-layered delivery system. The transdermal patch is then die cut to a suitable size.

The DIA cast on the liner, will then be applied directly on the skin, does not require as high of a drug loading as the second DIA. The second DIA acts as a reservoir and will diffuse drugs through the rate-controlling membrane after manufacture until equilibrium between the first DIA is achieved. Once applied, the second DIA will permeate drug in a zero-order rate through the membrane into the skin until drug reservoir is sufficiently depleted.

Example 9

N,N-dimethyltryptamine (DMT) freebase was dissolved in 25 mg/mL acetone. 7 mg/mL fumaric acid was added dropwise to precipitate DMT fumarate. The precipitate was washed with fresh acetone twice and dried under nitrogen.

DMT fumarate (18.0% w/w) was dissolved in deionized water (82.0% w/w) to afford a therapeutically effective aqueous gel vehicle for intranasal absorption at a suitable pH=6. The formulation of DMT fumarate gel can be administered via the nasal cavity in small volumes of between 0.04 and 0.50 mL for therapeutic effects. Potency analysis using tryptamine internal standard quantification revealed DMT freebase concentration of 135.5 mg/mL with no other degradation byproducts after storage for 106 days in dark conditions at room temperature.

Example 10

A Franz Cell apparatus was used to determine API release and permeability through a human skin mimic (Strat-M membrane, Millipore) and to compare patch effectiveness in Examples 1-8. The receiving well (10% ethanol in water) was kept at 32° C. throughout the experiment and all 10 mL were removed per sampling point. Drug flux was determined using the slope of zero-order permeated API over a specified time range. Potency analysis of API was accomplished using LC-MS while tryptamine (50 μg/mL) was added as an internal standard and used to quantify API with UV detection at 280 nm in Examples 1-9.

Example 11

Freebase 4-AcO-DMT (8% w/w) was dissolved in ethanol (4% w/w) and further added was povidone (2% w/w), butylated hydroxytoluene (1% w/w), and FD&C Blue No. 1. This solution was added to Ceolus KG 1000 microcrystalline cellulose (16% w/w) and mannitol (47% w/w) with simultaneous mixing and subsequent drying to form a homogenously coated powder. Further added was Prosolv HD 90 silicified microcrystalline cellulose (20% w/w), Cabosil silicon dioxide (1% w/w), and magnesium stearate (1% w/w) and blended to uniformity. Using a die set and sufficient force, a 250 mg tablet was formed for ingestion of 4-AcO-DMT for therapeutic use.

Example 12: 2-(2-chloro-1H-indol-3-yl)-N,N-dimethylethan-1-amine

A mixture of tryptamine hydrochloride salt (1 g, 5.1 mmol) and N-chlorosuccinimide (NCS, 0.69 g, 5.2 mmol) in acetic acid (50 mL) and formic acid (15 mL) was stirred for approximately 20 minutes. The product, 2-chloro-tryptamine (verified via 2D NMR spectroscopy), was dried and purified, and 211 mg (1.09 mmol) was further reacted with sodium cyanoborohydride (139.26 mg, 2.22 mmol) in methanol (21 mL) and formaldehyde (0.222 mL, 2.75 mmol) under nitrogen at 0° C. and stirred for 2.5 hours. The reaction was quenched with 1.0 M sodium hydroxide (27 mL) and extracted three times with methyl-tert-butyl-ether (MTBE). The residue was dried over sodium sulfate and concentrated down as a light brown oil/solid. Based on the LC-MS, ¹H and ¹³C NMR data, the final product contained majority 2-chloro-N,N-dimethyltryptamine. Product Formula C$_{12}$H$_{15}$N$_2$Cl m/z 222.0924, [M+H]$^+$ 223.0997

$^1$H NMR (600 MHz, DMSO-d$_6$) δ ppm 2.13 (s, 6H) 2.34-2.38 (m, 2H) 2.68-2.80 (m, 3H) 6.91-6.99 (m, 1H) 7.02 (t, J=7.54 Hz, 2H) 7.20 (d, J=7.99 Hz, 2H) 7.40 (d, J=7.81 Hz, 1H) 11.53 (br s, 1H)

Example 13: 2-(2-bromo-1H-indol-3-yl)-N,N-dimethylethan-1-amine

Previously documented methods were used to synthesize N,N-dimethyltryptamine (2.88 mmol) and dissolved in anhydrous acetonitrile (36 mL, 15 mg/mL) under inert conditions. This was combined with copper (II) bromide (1.93 g, 8.65 mmol) and stirred for 2 hours. The reaction was quenched with 40 mL of water and 100 mL EtOAc was added followed by 40 mL of saturated ammonium carbonate. The organic layer was washed and dried over sodium sulfate, filtered and concentrated down to a light brown oil (302.3 mg). The final major product, 2-bromo-N,N-dimethyltryptamine, was verified via LC-MS, 1D and 2D NMR spectroscopy. Product formula: C$_{12}$H$_{15}$N$_2$Br m/z 266.0419, [M+H]$^+$ 267.0491

$^1$H NMR (600 MHz, DMSO-d$_6$) δ ppm 2.21 (s, 6H) 2.38-2.47 (m, 2H) 2.73-2.88 (m, 3H) 6.93-7.03 (m, 1H) 7.03-7.11 (m, 1H) 7.28 (br d, J=7.99 Hz, 1H) 7.46-7.51 (m, 1H) 11.61 (br s, 1H)

Example 14: 2-bromo-3-(2-(dimethylamino)ethyl)-1H-indol-4-yl acetate

Previously documented methods were used to synthesize 4-acetoxy-N,N-dimethyltryptamine (14.9 mg, 0.06 mmol) and dissolved in anhydrous acetonitrile (1 mL) under inert conditions. Copper (II) bromide (40.5 mg, 0.18 mmol) was added and the reaction was stirred for 2 hours. Upon work-up, the major product, 2-bromo-4-acetoxy-N,N-dimethyltryptamine was verified via LC-MS and 1D NMR spectroscopy. Product formula: C$_{14}$H$_{17}$N$_2$O$_2$Br m/z 324.0473, [M+H]$^+$ 325.0546 $^1$H NMR (600 MHz, DMSO-d$_6$) δ ppm 2.21-2.25 (m, 13H) 2.32-2.39 (m, 12H) 2.71-2.75 (m, 3H) 6.74 (d, J=7.63 Hz, 1H) 7.06-7.10 (m, 2H) 7.18 (d, J=8.17 Hz, 2H) 11.91 (s, 1H)

Example 15: 2-(2-chloro-4-methoxy-1H-indol-3-yl)-N,N-dimethylethan-1-amine

Previously documented methods were used to synthesize 4-methoxy-N,N-dimethyltryptamine (130 mg, 0.6 mmol) and dissolved in anhydrous acetonitrile (3.6 mL). Copper (II) chloride (241 mg, 1.8 mmol) was added and stirred overnight under inert atmosphere. Quenched with water (14 mL) and extracted three times with EtOAc and washed with saturated ammonium carbonate. The organic layer was dried over sodium sulfate, filtered and concentrated to an orange semi-solid (38.2 mg, 25% yield). This was purified via HPLC to produce 2-chloro-4-methoxy-N,N-dimethyltryptamine and verified via LC-MS, 1D and 2D NMR spectroscopy.

Product formula: C$_{13}$H$_{17}$N$_2$OCl m/z 252.1029, [M+H]$^+$ 253.1102 $^1$H NMR (600 MHz, DMSO-d$_6$) δ ppm 2.27-2.39 (m, 14H) 2.50-2.60 (m, 6H) 2.89-3.05 (m, 5H) 3.84-3.99 (m, 9H) 6.54-6.66 (m, 2H) 6.92 (d, J=8.17 Hz, 1H) 7.03-7.19 (m, 2H) 11.71 (s, 1H)

Example 16: 1-(3-(2-(dimethylamino)ethyl)-1H-indol-4-yl)-N-methylmethanesulfonamide The nitro group of N-methyl-3-nitrobenzenesulfonamide will be reduced via palladium on carbon (H$_2$/Pd/C) in ethanol solvent and aqueous HCl to the subsequent aniline. This product will be treated with sodium nitrite to give the diazonium salt and subsequently reduced to the hydrazine with SnCl$_2$, all at 0° C. The hydrazone will be generated upon condensation with 4,4-dimethyoxy-N,N-dimethylbutylamine in aqueous hydrochloric acid. The final product will be produced via the Fischer indole reaction, where the hydrazone will be reacted with polyphosphoric acid in refluxing chloroform to initiate cyclization.

This compound can be further halogenated at the C-2 position following the Copper (II) halide protocols of previous examples.

Example 17: Computational Analysis

Six distinct receptor models were tested depending on the documented crystal structures in the RCSB Protein Data Bank (PDB) for various serotonin receptors and sigma-1. These receptor structures include 5-HT$_{2A}$, 5-HT$_{2B}$, 5-HT$_{1B}$, and σ$_1$ (PDB ID's also shown in column headings).

For each static protein structure, the PDB files of crystal structures containing bound ligands most chemically similar to the tryptamine scaffold were used for most accuracy where possible (e.g. LSD or ergotamine-bound). The overall workflow was performed using various aspects of the Schrödinger software suite. The 3D SMILES for each ligand was uploaded following literature recommended protonation and/or charge for tryptamines and various conformers were generated and minimized using Schrödinger LigPrep. A final list of compounds were screened with Glide scores being generated by Schrödinger Glide including the structures listed in Table 3. Validation of this technique was done by including known agonists of 5-HT and σ$_1$ receptors and compared to experimental binding assay data. The docking scores of the known agonists and the experimental data were comparable and within the experimental error for activity. For example, the (+)-LSD enantiomer shows greater activity in vitro at the 5-HT$_{2A}$ receptor than the (−)-LSD enantiomer, and our computationally rendered values show the same trend in activity.

TABLE 3

Virtual Docking Glide Scores of Compounds in Table (1)

| | Compound Name | 6WGT (5-HT$_{2A}$) | 5TVN (5-HT$_{2B}$) | 4IAR (5-HT$_{1B}$) | 5HK2 (Sigma-1) | 5HK1 (Sigma-1) | 4IB4 (5-HT$_{2B}$) |
|---|---|---|---|---|---|---|---|
| 1 | 2-(2-chloro-1H-indol-3-yl)-N,N-dimethylethan-1-amine | −9.11 | −7.09 | −6.27 | −9.2 | −8.04 | −8.82 |
| 2 | 2-(2-bromo-1H-indol-3-yl)-N,N-dimethylethan-1-amine | −9.12 | −8.85 | −7.19 | −9.39 | −7.4 | −8.91 |

TABLE 3-continued

Virtual Docking Glide Scores of Compounds in Table (1)

| Compound | Name | 6WGT (5-HT2$_A$) | 5TVN (5-HT2$_B$) | 4IAR (5-HT1$_B$) | 5HK2 (Sigma-1) | 5HK1 (Sigma-1) | 4IB4 (5-HT2$_B$) |
|---|---|---|---|---|---|---|---|
| 3 | 2-chloro-3-(2-(dimethylamino) ethyl)-1H-indol-4-yl acetate | Z-4.92 | −6.39 | −5.31 | −10.74 | −9.08 | −8.79 |
| 4 | 2-bromo-3-(2-(dimethylamino) ethyl)-1H-indol-4-yl acetate | −10.89 | −6.97 | −5.89 | −10.72 | −9.42 | −8.9 |
| 5 | 2-chloro-3-(2-(dimethylamino) ethyl)-1H-indol-4-yl hydrogen phosphate | −9.28 | −3.54 | −5.94 | −7.5 | −10.56 | −8.48 |
| 6 | 2-bromo-3-(2-(dimethylamino) ethyl)-1H-indol-4-yl hydrogen phosphate | −7.84 | −3.4 | −5.68 | −9.58 | −10.17 | −8.71 |
| 7 | 2-bromo-3-(2-(dimethylamino) ethyl)-1H-indol-4-ol | −8.76 | −7.46 | −6.73 | −8.05 | −9.19 | −8.53 |
| 8 | 2-chloro-3-(2-(dimethylamino) ethyl)-1H-indol-4-ol | −8.74 | −6.49 | −6.81 | −7.68 | −8.98 | −8.44 |
| 9 | 1-(2-chloro-3-(2-(dimethylamino) ethyl)-1H-indol-4-yl)-N-methylmethanesulfonamide | −6.72 | −6.64 | −4.43 | −7.69 | −10.55 | −5.96 |
| 10 | 1-(2-bromo-3-(2-(dimethylamino) ethyl)-1H-indol-4-yl)-N-methylmethanesulfonamide | −3.85 | −6.37 | −5.87 | −10.83 | −10.46 | −8.54 |
| 11 | 1-(3-(2-(dimethylamino) ethyl)-1H-indol-4-yl)-N-methylmethanesulfonamide | −7.53 | −7.47 | −6.92 | −11.54 | −10.41 | −8.07 |
| 12 | 2-(2-chloro-4-methoxy-1H-indol-3-yl)-N,N-dimethylethan-1-amine | −8.86 | −5.81 | −6.26 | −9.26 | −10.95 | −8.37 |
| 13 | 2-(2-bromo-4-methoxy-1H-indol-3-yl)-N,N-dimethylethan-1-amine | −8.77 | −6.43 | −6.24 | −8.51 | −9.03 | −8.49 |
| 14 | (R)-1-(2-chloro-1H-indol-3-yl)propan-2-amine | −7.71 | −6.36 | −6.46 | −8.31 | −7.89 | −8.63 |
| 15 | (R)-1-(2-chloro-1H-indol-3-yl)-N-methylpropan-2-amine | −8.76 | −6.77 | −6.31 | −8.04 | −8.78 | −9 |
| 16 | (R)-1-(2-chloro-1H-indol-3-yl)-N,N-dimethylpropan-2-amine | −9.55 | −6.15 | −6.9 | −9.04 | −8.23 | −8.91 |
| 17 | (S)-1-(2-chloro-1H-indol-3-yl)-N,N-dimethylpropan-2-amine | −9.07 | −7.06 | −7.48 | −9.05 | −7.52 | −8.69 |
| 18 | (S)-1-(2-chloro-1H-indol-3-yl)propan-2-amine | −7.98 | −6.52 | −7.19 | −7.49 | −7.69 | −8.96 |
| 19 | (S)-1-(2-chloro-1H-indol-3-yl)-N-methylpropan-2-amine | −8.74 | −6.74 | −7.2 | −9.76 | −7.62 | −9.28 |
| 20 | (R)-1-(2-bromo-1H-indol-3-yl)propan-2-amine | −7.93 | −6.58 | −6.66 | −8.25 | −8.06 | −8.64 |
| 21 | (R)-1-(2-bromo-1H-indol-3-yl)-N-methylpropan-2-amine | −10.36 | −6.7 | −7.31 | −8.2 | −8.81 | −8.99 |
| 22 | (R)-1-(2-bromo-1H-indol-3-yl)-N,N-dimethylpropan-2-amine | −8.75 | −6.29 | −7.1 | −9.02 | −7.89 | −8.82 |
| 23 | (S)-1-(2-bromo-1H-indol-3-yl)-N,N-dimethylpropan-2-amine | −9.23 | −7.13 | −7.44 | −9.31 | −6.66 | −8.8 |
| 24 | (S)-1-(2-bromo-1H-indol-3-yl)propan-2-amine | Z-9.27 | −6.85 | −7.2 | −8.27 | −8.3 | −8.14 |
| 25 | (S)-1-(2-bromo-1H-indol-3-yl)-N-methylpropan-2-amine | −9.06 | −7.01 | −7.48 | −8.12 | −7.7 | −9.09 |
| 26 | 2-(2-chloro-1H-indol-3-yl)-N,N-diethylethan-1-amine | −10.49 | −7.5 | −7.53 | −9.91 | −8.49 | −8.93 |
| 27 | N-(2-(2-chloro-1H-indol-3-yl)ethyl)-N-isopropylpropan-2-amine | −9.68 | −7.61 | −6.39 | −8.91 | −9.5 | −9.44 |
| 28 | N-(2-(2-chloro-1H-indol-3-yl)ethyl)-N-vinylethenamine | −9.46 | −6.84 | −7.1 | −9.33 | −8.52 | −8.76 |
| 29 | 2-(2-bromo-1H-indol-3-yl)-N,N-diethylethan-1-amine | −9.59 | −7.57 | −7.63 | −8.88 | −9.63 | −9.5 |
| 30 | N-(2-(2-bromo-1H-indol-3-yl)ethyl)-N-isopropylpropan-2-amine | −7.42 | −7.92 | −6.01 | −9.25 | −9.75 | −9.4 |
| 31 | N-(2-(2-bromo-1H-indol-3-yl)ethyl)-N-vinylethenamine | −9.22 | −7.27 | −7.75 | −9.34 | −8.5 | −8.98 |

The present disclosure has been described in connection with certain embodiments and examples; however, unless otherwise indicated, the claimed invention should not be unduly limited to such specific embodiments and examples.

The invention claimed is:

1. A pharmaceutical product for delivery across a mucosal membrane, wherein said product comprises:
    an active ingredient, wherein the active ingredient is DMT or DMT fumarate, or a pharmaceutically acceptable salt of DMT, wherein the active ingredient is present in a therapeutically effective amount; and
    a pharmaceutically acceptable carrier,
    wherein the active ingredient is capable of crossing a mucosal membrane.

2. The pharmaceutical product of claim 1, wherein the therapeutically effective amount is about 0.01%-about 20% (w/w).

3. The pharmaceutical product of claim 1, wherein the mucosal membrane is sublingual, buccal, nasal, or oral.

4. The pharmaceutical product of claim 3, wherein the pharmaceutical product is in the form of a solution, a gel, a suspension, an emulsion, liposome, or microparticles.

5. The pharmaceutical product of claim 4, wherein the pharmaceutically acceptable carrier is an adhesive polymer.

6. The pharmaceutical product of claim 4, wherein the product is in the form of a spray.

7. The pharmaceutical product of claim 4, wherein the product is in the form of a film.

8. The pharmaceutical product of claim 1, wherein the active ingredient is DMT or a pharmaceutically acceptable salt thereof.

9. The pharmaceutical product of claim 1, wherein the active ingredient is DMT fumarate.

10. The pharmaceutical product of claim 8, further comprising an MAOI.

11. The pharmaceutical product of claim 10, wherein the MAOI is selected from the group consisting of harmala alkaloids, harmine, harmane, harmaline, hydrazine, iproniazid, isocarboxazid, nialamide, phenelzine, hydracarbazine, tranylcypromine, bifemelane, moclobemide, pirlindole, toloxatone, rasagiline, selegiline, and safinamide.

12. The pharmaceutical product of claim 9, further comprising an MAOI.

13. The pharmaceutical product of claim 12, wherein the MAOI is selected from the group consisting of harmala alkaloids, harmine, harmane, harmaline, hydrazine, iproniazid, isocarboxazid, nialamide, phenelzine, hydracarbazine, tranylcypromine, bifemelane, moclobemide, pirlindole, toloxatone, rasagiline, selegiline, and safinamide.

14. The pharmaceutical product of claim 11, wherein the MAOI is harmine.

15. The pharmaceutical product of claim 13, wherein the MAOI is harmine.

16. The pharmaceutical product of claim 1, wherein the pharmaceutical product is an aqueous gel in an amount between about 0.04 ml and about 0.50 mL.

17. The pharmaceutical product of claim 16, wherein the active ingredient is DMT or a pharmaceutically acceptable salt thereof.

18. The pharmaceutical product of claim 17, wherein the active ingredient is DMT fumarate.

19. The pharmaceutical product of claim 8, wherein the pharmaceutical product is in the form of a sublingual strip.

20. The pharmaceutical product of claim 9, wherein the pharmaceutical product is in the form of a sublingual strip.

* * * * *